(12) United States Patent
Kuyu et al.

(10) Patent No.: US 9,052,440 B2
(45) Date of Patent: *Jun. 9, 2015

(54) CHAIN-EXTENDED POLYSILOXANE CROSSLINKERS WITH DANGLING HYDROPHILIC POLYMER CHAINS

(71) Applicant: Novartis AG, Basel (CH)

(72) Inventors: Selma Kuyu, Duluth, GA (US); Dawn Alison Smith, Rotorua (NZ); Jinyu Huang, Suwanee, GA (US); Frank Chang, Cumming, GA (US); Robert Scott, Alpharetta, GA (US); Arturo Norberto Medina, Suwanee, GA (US); Venkat Shankar, Suwanee, GA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/453,021

(22) Filed: Aug. 6, 2014

(65) Prior Publication Data

US 2014/0350124 A1 Nov. 27, 2014

Related U.S. Application Data

(62) Division of application No. 13/253,177, filed on Oct. 5, 2011, now Pat. No. 8,835,525.

(60) Provisional application No. 61/390,464, filed on Oct. 6, 2010, provisional application No. 61/422,672, filed on Dec. 14, 2010.

(51) Int. Cl.
| | |
|---|---|
| A61K 47/34 | (2006.01) |
| C08G 77/38 | (2006.01) |
| G02B 1/04 | (2006.01) |
| C08G 77/42 | (2006.01) |
| C08G 77/442 | (2006.01) |
| C08G 77/46 | (2006.01) |
| C08L 83/10 | (2006.01) |
| C08G 77/20 | (2006.01) |

(52) U.S. Cl.
CPC ............... *G02B 1/043* (2013.01); *C08G 77/20* (2013.01); *C08G 77/42* (2013.01); *C08G 77/442* (2013.01); *C08G 77/46* (2013.01); *C08L 83/10* (2013.01); *A61K 47/34* (2013.01); *C08G 77/38* (2013.01); *G02B 2207/109* (2013.01)

(58) Field of Classification Search
CPC ................... C08L 83/12–83/14; C08G 77/20; C08G 77/42
USPC ............................ 523/107; 525/479; 424/429
See application file for complete search history.

(56) References Cited

U.S. PATENT DOCUMENTS

| | | |
|---|---|---|
| 4,042,552 A | 8/1977 | Grucza |
| 4,045,547 A | 8/1977 | Le Boeuf et al. |
| 4,136,250 A | 1/1979 | Mueller et al. |
| 4,153,641 A | 5/1979 | Deichert et al. |
| 4,182,822 A | 1/1980 | Chang |
| 4,189,546 A | 2/1980 | Deichert et al. |
| 4,245,069 A | 1/1981 | Covington |
| 4,254,248 A | 3/1981 | Friends et al. |
| 4,259,467 A | 3/1981 | Keogh et al. |
| 4,260,725 A | 4/1981 | Keogh et al. |
| 4,261,875 A | 4/1981 | LeBoeuf |
| 4,276,402 A | 6/1981 | Chromecek et al. |
| 4,312,575 A | 1/1982 | Peyman et al. |
| 4,327,203 A | 4/1982 | Deichert et al. |
| 4,341,889 A | 7/1982 | Deichert et al. |
| 4,343,927 A | 8/1982 | Chang |
| 4,355,147 A | 10/1982 | Deichert et al. |
| 4,444,711 A | 4/1984 | Schad |
| 4,460,534 A | 7/1984 | Boehm et al. |
| 4,467,082 A | 8/1984 | Shirahata et al. |
| 4,485,236 A | 11/1984 | Rasmussen |
| 4,486,577 A | 12/1984 | Mueller et al. |
| 4,543,398 A | 9/1985 | Bany et al. |
| 4,605,712 A | 8/1986 | Mueller et al. |
| 4,632,844 A | 12/1986 | Yanagihara et al. |
| 4,661,575 A | 4/1987 | Tom |
| 4,666,953 A | 5/1987 | Klemiarczyk et al. |
| 4,684,538 A | 8/1987 | Klemarczyk |

(Continued)

FOREIGN PATENT DOCUMENTS

| | | |
|---|---|---|
| EP | 0379146 B1 | 7/1990 |
| EP | 0425436 A2 | 5/1991 |
| EP | 455585 A1 | 6/1991 |
| EP | 0584826 B1 | 3/1994 |
| EP | 0677561 A1 | 10/1995 |
| EP | 0584764 B1 | 3/1997 |
| EP | 862068 A2 | 9/1998 |
| EP | 0932635 B1 | 8/1999 |
| EP | 0958315 B1 | 11/1999 |
| EP | 0961941 B1 | 12/1999 |
| EP | 1197782 A1 | 4/2002 |
| EP | 1754728 B1 | 2/2007 |

(Continued)

OTHER PUBLICATIONS

Wang, YF, Amphilic Poly(acrylamide)s Having Saturated and Unsaturated Dialkyl Chains and Phosphatidylcholine Groups and the Side Chains; Macromolecules, 1996; 29; 5810-5817.

Authors: Erik B. Berda and Kenneth B. Wagener Title: Probing the Effects of Hydrophilic Branch Size, Distribution, and Connectivity in Amphiphilic Polyethylene Published: Macromolecular Chemistry and Physics, (2008) 209, pp. 1601-1611.

*Primary Examiner* — Richard Schnizer
*Assistant Examiner* — Alma Pipic
(74) *Attorney, Agent, or Firm* — Jian Zhou

(57) ABSTRACT

The invention provide a class of linear chain-extended polysiloxane crosslinkers which comprises two terminal ethylenically unsaturated groups, at least two polysiloxane segments, and dangling hydrophilic polymer chains each covalently attached to a divalent organic radical separating each pair of adjacent polysiloxane segments. The present invention is also related to a polymer comprising crosslinking units derived from chain-extended polysiloxane crosslinker of the invention and to ophthalmic lenses comprising such a polymer.

5 Claims, No Drawings

(56) References Cited

U.S. PATENT DOCUMENTS

| | | |
|---|---|---|
| 4,703,097 A | 10/1987 | Wingler et al. |
| 4,711,943 A | 12/1987 | Harvey, III |
| 4,833,218 A | 5/1989 | Lee |
| 4,837,289 A | 6/1989 | Mueller et al. |
| 4,954,586 A | 9/1990 | Toyoshima |
| 4,954,587 A | 9/1990 | Mueller |
| 4,983,702 A | 1/1991 | Mueller |
| 5,010,141 A | 4/1991 | Mueller |
| 5,034,461 A | 7/1991 | Lai |
| 5,039,761 A | 8/1991 | Ono |
| 5,070,169 A | 12/1991 | Robertson |
| 5,070,170 A | 12/1991 | Robertson |
| 5,070,215 A | 12/1991 | Bambury |
| 5,079,319 A | 1/1992 | Mueller |
| 5,164,462 A | 11/1992 | Yang |
| 5,194,556 A | 3/1993 | Mueller |
| 5,198,477 A | 3/1993 | von der Haegen |
| 5,219,965 A | 6/1993 | Valint, Jr. |
| 5,224,957 A | 7/1993 | Gasser |
| 5,227,432 A | 7/1993 | Jung |
| 5,244,981 A | 9/1993 | Seidner |
| 5,314,960 A | 5/1994 | Spinelli |
| 5,314,961 A | 5/1994 | Anton |
| 5,331,067 A | 7/1994 | Seidner |
| 5,346,946 A | 9/1994 | Yokoyama |
| 5,352,753 A | 10/1994 | Yang |
| 5,358,995 A | 10/1994 | Lai |
| 5,376,637 A | 12/1994 | Sawai |
| 5,387,632 A | 2/1995 | Lai |
| 5,416,132 A | 5/1995 | Yokoyama |
| 5,423,158 A | 6/1995 | Vora |
| 5,426,158 A | 6/1995 | Mueller |
| 5,449,729 A | 9/1995 | Lai |
| 5,451,617 A | 9/1995 | Lai |
| 5,466,768 A | 11/1995 | Yang |
| 5,480,927 A | 1/1996 | Janssen |
| 5,480,946 A | 1/1996 | Mueller |
| 5,486,579 A | 1/1996 | Lai |
| 5,489,474 A | 2/1996 | Shinoda |
| 5,508,317 A | 4/1996 | Müller |
| 5,512,205 A | 4/1996 | Lai |
| 5,527,925 A | 6/1996 | Chabrecek |
| 5,559,163 A | 9/1996 | Dawson |
| 5,583,163 A | 12/1996 | Müller |
| 5,612,389 A | 3/1997 | Chabrecek |
| 5,612,391 A | 3/1997 | Chabrecek |
| 5,621,018 A | 4/1997 | Chabrecek |
| 5,637,726 A | 6/1997 | Collins |
| 5,663,288 A | 9/1997 | Shinoda |
| 5,665,840 A | 9/1997 | Pöhlmann |
| 5,681,871 A | 10/1997 | Molock |
| 5,712,356 A | 1/1998 | Bothe |
| 5,723,512 A | 3/1998 | Leppard |
| 5,729,322 A | 3/1998 | Collins |
| 5,760,100 A | 6/1998 | Nicolson |
| 5,767,169 A | 6/1998 | Leppard |
| 5,789,464 A | 8/1998 | Müller |
| 5,843,346 A | 12/1998 | Morrill |
| 5,849,810 A | 12/1998 | Müller |
| 5,849,811 A | 12/1998 | Nicolson |
| 5,849,841 A | 12/1998 | Mühlebach |
| 5,866,635 A | 2/1999 | Collins |
| 5,894,002 A | 4/1999 | Boneberger |
| 5,914,355 A | 6/1999 | Künzler |
| 5,959,117 A | 9/1999 | Ozark |
| 5,962,548 A | 10/1999 | Vanderlaan |
| 5,965,776 A | 10/1999 | Leppard |
| 5,981,615 A | 11/1999 | Meijs |
| 5,981,669 A | 11/1999 | Valint, Jr. |
| 5,981,675 A | 11/1999 | Valint, Jr. |
| 5,989,462 A | 11/1999 | Buazza |
| 5,994,488 A | 11/1999 | Yokota |
| 5,998,498 A | 12/1999 | Vanderlaan |
| 6,015,842 A | 1/2000 | LeBoeuf |
| 6,015,874 A | 1/2000 | Hiratani |
| 6,020,445 A | 2/2000 | Vanderlaan |
| 6,020,528 A | 2/2000 | Leppard |
| 6,036,891 A | 3/2000 | Liao |
| 6,039,913 A | 3/2000 | Hirt |
| 6,096,846 A | 8/2000 | Oda |
| 6,136,880 A | 10/2000 | Snowwhite |
| 6,149,692 A | 11/2000 | Lally |
| 6,153,760 A | 11/2000 | Künzler |
| 6,162,844 A | 12/2000 | Lally |
| 6,165,408 A | 12/2000 | Steinmann |
| 6,204,300 B1 | 3/2001 | Kageoka |
| 6,204,306 B1 | 3/2001 | Chabrecek |
| 6,218,463 B1 | 4/2001 | Molock |
| 6,218,508 B1 | 4/2001 | Kragh |
| 6,221,303 B1 | 4/2001 | Steinmann |
| 6,252,032 B1 | 6/2001 | Van Antwerp |
| 6,284,813 B1 | 9/2001 | Leppard |
| 6,303,687 B1 | 10/2001 | Müller |
| 6,310,215 B1 | 10/2001 | Iwamoto |
| 6,312,706 B1 | 11/2001 | Lai |
| 6,329,485 B1 | 12/2001 | Vanderbilt |
| 6,342,570 B1 | 1/2002 | Bothe |
| 6,359,024 B2 | 3/2002 | Lai |
| 6,359,025 B1 | 3/2002 | Snowwhite |
| 6,361,925 B1 | 3/2002 | Leppard |
| 6,367,929 B1 | 4/2002 | Maiden |
| 6,376,568 B1 | 4/2002 | Baudin |
| 6,451,871 B1 | 9/2002 | Winterton |
| 6,465,538 B2 | 10/2002 | Lai |
| 6,472,489 B1 | 10/2002 | Stockinger |
| 6,479,587 B1 | 11/2002 | Stockinger |
| 6,492,478 B1 | 12/2002 | Steinmann |
| 6,596,294 B2 | 7/2003 | Lai |
| 6,627,124 B1 | 9/2003 | Herbrechtsmeier |
| 6,638,991 B2 | 10/2003 | Baba |
| 6,657,029 B2 | 12/2003 | Vanderbilt |
| 6,657,030 B2 | 12/2003 | Vanderbilt |
| 6,657,032 B2 | 12/2003 | Vanderbilt |
| 6,673,886 B2 | 1/2004 | Vanderbilt |
| 6,693,141 B2 | 2/2004 | Baudin |
| 6,713,583 B2 | 3/2004 | Liao |
| 6,719,929 B2 | 4/2004 | Winterton |
| 6,762,264 B2 | 7/2004 | Künzler |
| 6,767,169 B2 | 7/2004 | Zhan |
| 6,776,934 B2 | 8/2004 | Lai |
| 6,793,973 B2 | 9/2004 | Winterton |
| 6,800,225 B1 | 10/2004 | Hagmann |
| 6,811,804 B2 | 11/2004 | Patel |
| 6,811,805 B2 | 11/2004 | Gilliard |
| 6,822,016 B2 | 11/2004 | McCabe |
| 6,849,671 B2 | 2/2005 | Steffen |
| 6,852,353 B2 | 2/2005 | Qiu |
| 6,852,793 B2 | 2/2005 | Salamone |
| 6,858,218 B2 | 2/2005 | Lai |
| 6,884,457 B2 | 4/2005 | Gilliard |
| 6,896,926 B2 | 5/2005 | Qiu |
| 6,926,965 B2 | 8/2005 | Qiu |
| 6,940,580 B2 | 9/2005 | Winterton |
| 6,943,203 B2 | 9/2005 | Vanderlaan |
| 6,995,192 B2 | 2/2006 | Phelan |
| 7,040,756 B2 | 5/2006 | Qiu |
| 7,052,131 B2 | 5/2006 | McCabe |
| 7,071,274 B2 | 7/2006 | Fujisawa |
| 7,078,074 B2 | 7/2006 | Matsuzawa |
| 7,091,283 B2 | 8/2006 | Müller |
| 7,112,641 B2 | 9/2006 | Fujisawa |
| 7,214,809 B2 | 5/2007 | Zanini |
| 7,238,750 B2 | 7/2007 | Müller |
| 7,247,692 B2 | 7/2007 | Laredo |
| 7,249,848 B2 | 7/2007 | Laredo |
| 7,256,246 B2 | 8/2007 | Kindt-Larsen |
| 7,279,507 B2 | 10/2007 | Hu |
| 7,384,590 B2 | 6/2008 | Kelly |
| 7,387,759 B2 | 6/2008 | Kelly |
| 7,396,890 B2 | 7/2008 | Zanini |
| 7,416,737 B2 | 8/2008 | Alvarez-Carrigan |
| 7,423,108 B2 | 9/2008 | Kunzler |
| 7,461,937 B2 | 12/2008 | Steffen |
| 7,468,397 B2 | 12/2008 | Schorzman |

(56) References Cited

U.S. PATENT DOCUMENTS

| | | |
|---|---|---|
| 7,521,488 B2 | 4/2009 | Steffen |
| 7,521,519 B1 | 4/2009 | Hirt |
| 7,550,519 B2 | 6/2009 | Phelan |
| 7,649,058 B2 | 1/2010 | McCabe |
| 7,666,921 B2 | 2/2010 | McCabe |
| 7,691,916 B2 | 4/2010 | McCabe |
| 8,124,668 B2 | 2/2012 | Baba |
| 2001/0037001 A1 | 11/2001 | Muller |
| 2002/0042022 A1 | 4/2002 | Leppard |
| 2002/0107297 A1 | 8/2002 | Baudin |
| 2002/0107324 A1 | 8/2002 | Vanderlaan |
| 2002/0198280 A1 | 12/2002 | Baba |
| 2003/0044447 A1 | 3/2003 | Zanini |
| 2003/0125498 A1 | 7/2003 | McCabe |
| 2003/0162862 A1 | 8/2003 | McCabe |
| 2004/0082680 A1 | 4/2004 | Phelan |
| 2004/0115242 A1 | 6/2004 | Meyers |
| 2004/0150788 A1 | 8/2004 | Anderson |
| 2004/0151755 A1 | 8/2004 | Rathore |
| 2004/0186248 A1 | 9/2004 | Vanderlaan |
| 2004/0209973 A1 | 10/2004 | Steffen |
| 2004/0213827 A1 | 10/2004 | Enns |
| 2005/0055090 A1 | 3/2005 | Lai |
| 2005/0113549 A1 | 5/2005 | Devlin |
| 2005/0117112 A1 | 6/2005 | Nayiby |
| 2005/0154080 A1 | 7/2005 | McCabe |
| 2005/0159502 A1 | 7/2005 | Steffen |
| 2005/0179862 A1 | 8/2005 | Steffen |
| 2005/0237483 A1 | 10/2005 | Phelan |
| 2005/0260249 A1 | 11/2005 | Neely |
| 2006/0007391 A1 | 1/2006 | McCabe |
| 2006/0036052 A1 | 2/2006 | Kindt-Larsen |
| 2006/0069178 A1 | 3/2006 | Rastogi |
| 2006/0142410 A1 | 6/2006 | Baba |
| 2006/0235162 A1 | 10/2006 | Muller |
| 2006/0252850 A1 | 11/2006 | Jani |
| 2007/0043140 A1 | 2/2007 | Lorenz |
| 2007/0092830 A1 | 4/2007 | Lai |
| 2007/0092831 A1 | 4/2007 | Lai |
| 2007/0138692 A1 | 6/2007 | Ford |
| 2007/0142551 A1 | 6/2007 | Kunzler |
| 2007/0142584 A1 | 6/2007 | Schorzman |
| 2007/0160643 A1 | 7/2007 | Schorzman |
| 2007/0160649 A1 | 7/2007 | Schorzman |
| 2007/0161810 A1 | 7/2007 | Schorzman |
| 2007/0229757 A1 | 10/2007 | McCabe |
| 2007/0242215 A1 | 10/2007 | Schorzman |
| 2008/0000201 A1 | 1/2008 | Schorzman |
| 2008/0004413 A1 | 1/2008 | Schorzman |
| 2008/0004414 A1 | 1/2008 | Schorzman |
| 2008/0015282 A1 | 1/2008 | McCabe |
| 2008/0015315 A1 | 1/2008 | Chang |
| 2008/0076897 A1 | 3/2008 | Kunzler |
| 2008/0143003 A1 | 6/2008 | Phelan |
| 2008/0143958 A1 | 6/2008 | Medina |
| 2008/0174035 A1 | 7/2008 | Winterton |
| 2008/0231798 A1 | 9/2008 | Zhou |
| 2008/0234457 A1 | 9/2008 | Zhou |
| 2008/0274207 A1 | 11/2008 | Nayiby |
| 2008/0299179 A1 | 12/2008 | Rathore |
| 2008/0316424 A1 | 12/2008 | McCabe |
| 2009/0005528 A1 | 1/2009 | Fujisawa |
| 2009/0059164 A1 | 3/2009 | Steffen |
| 2009/0091704 A1 | 4/2009 | Steffen |
| 2009/0230575 A1 | 9/2009 | Liu |
| 2009/0252868 A1 | 10/2009 | Phelan |
| 2009/0276042 A1 | 11/2009 | Hughes |
| 2010/0084775 A1 | 4/2010 | McCabe |
| 2010/0120938 A1 | 5/2010 | Phelan |
| 2010/0133710 A1 | 6/2010 | McCabe |
| 2010/0152084 A1 | 6/2010 | Rathore |
| 2010/0168359 A1 | 7/2010 | Domschke |
| 2012/0088843 A1 | 4/2012 | Chang |
| 2012/0088844 A1 | 4/2012 | Kuyu |
| 2012/0088861 A1 | 4/2012 | Huang et al. |

FOREIGN PATENT DOCUMENTS

| | | |
|---|---|---|
| GB | 2292740 A | 3/1996 |
| GB | 2310855 A | 9/1997 |
| JP | 2004085655 A2 | 3/2004 |
| WO | 9628762 | 9/1996 |
| WO | 9628762 A1 | 9/1996 |
| WO | 9805690 | 2/1998 |
| WO | 9805690 A1 | 2/1998 |
| WO | 9847954 | 10/1998 |
| WO | 9847954 A1 | 10/1998 |
| WO | 9933894 | 7/1999 |
| WO | 9933894 A1 | 7/1999 |
| WO | 0031150 | 6/2000 |
| WO | 0031150 A1 | 6/2000 |
| WO | 0059970 | 10/2000 |
| WO | 0059970 A1 | 10/2000 |
| WO | 2007128051 A1 | 11/2007 |
| WO | 2007146299 A2 | 12/2007 |
| WO | 2007146312 A2 | 12/2007 |
| WO | 2008116131 A2 | 9/2008 |

CHAIN-EXTENDED POLYSILOXANE CROSSLINKERS WITH DANGLING HYDROPHILIC POLYMER CHAINS

This application is a division of application Ser. No. 13/253,177 filed 5 Oct. 2011, now U.S. Pat. No. 8,835,525, which claims the benefits under 35 USC §119 (e) of U.S. provisional application No. 61/390,464 filed 6 Oct. 2010 and 61/422,672 filed 14 Dec. 2010, incorporated by reference in their entireties.

The present invention is related to a class of polymerizable chain-extended polysiloxane with dangling hydrophilic polymer chains and uses thereof. The present invention is also related to a polymer which is a polymerization product of a polymerizable chain-extended polysiloxane of the invention with one or more other polymerizable compounds and to silicone hydrogel contact lenses made from a lens formulation including a polymerizable chain-extended polysiloxane of the invention.

BACKGROUND

In recent years, soft silicone hydrogel contact lenses become more and more popular because of their high oxygen permeability and comfort. One of lens forming materials widely used in making silicone hydrogel contact lenses is polymerizable polysiloxane. The main function of the polymerizable polysiloxane is to provide high oxygen permeability to resultant contact lenses.

However, it is known that polysiloxanes has a great tendency to migrate onto the surface of a substrate made of material containing polysiloxanes to minimize the surface energy of the substrate. Contact lenses with a high amount of polymerizable polysiloxane(s) generally exhibit poor wettability and generally require a surface treatment.

In addition, because of its hydrophobic nature, a polymerizable polysiloxane is generally not compatible with hydrophilic components in a lens formulation, including, e.g., hydroxyethylmethacrylate, hydroxyethylacrylate, N,N-dimethylacrylamide, N-vinylpyrrolidone, or an internal wetting agent. It would be difficult to obtain homogeneous lens formulations.

Therefore, there is still a need for polymerizable polysiloxane which are relatively more compatible with the hydrophilic components of a lens formulation for making silicone hydrogel contact lenses and can improve the surface wettability of contact lenses made from such lens formulation.

SUMMARY OF THE INVENTION

The present invention, in one aspect, provides a linear chain-extended polysiloxane crosslinker which comprises two terminal ethylenically unsaturated groups, at least two polysiloxane segments, and dangling hydrophilic polymer chains each covalently attached to a divalent organic radical separating each pair of adjacent polysiloxane segments.

In another aspect, the invention provides a polymer comprising polymer units derived from at least one polymerizable chain-extended polysiloxane crosslinker of the invention.

In a further aspect, the invention provides silicone hydrogel contact lens, which comprises: a polymeric material that is obtained by polymerizing a lens-forming material including a polymerizable chain-extended polysiloxane crosslinker of the invention in a mold.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" or "hydrogel material" refers to a polymeric material which can absorb at least 10 percent by weight of water when it is fully hydrated.

A "silicone hydrogel" refers to a silicone-containing hydrogel obtained by copolymerization of a polymerizable composition comprising at least one silicone-containing vinylic monomer or crosslinker or at least one actinically-crosslinkable silicone-containing prepolymer.

"Hydrophilic," as used herein, describes a material or portion thereof that will more readily associate with water than with lipids.

A "monomer" refers to a compound that can be polymerized chemically, actinically or thermally.

A "vinylic monomer", as used herein, refers to a monomer that has one sole ethylenically unsaturated group and can be polymerized actinically or thermally.

The term "olefinically unsaturated group" or "ethylenically unsaturated group" is employed herein in a broad sense and is intended to encompass any groups containing at least one >C=C< group. Exemplary ethylenically unsaturated groups include without limitation

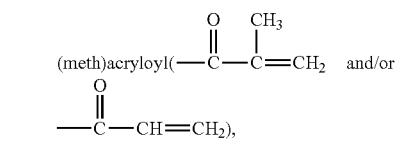

allyl, vinyl, styrenyl, or other C=C containing groups.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionizing radiation (e.g. gamma ray or X-ray irradiation), microwave irradiation, and the like. Thermal curing or actinic curing methods are well-known to a person skilled in the art.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which as a homopolymer typically yields a polymer that is water-soluble or can absorb at least 10 percent by weight water.

A "hydrophobic vinylic monomer", as used herein, refers to a vinylic monomer which as a homopolymer typically yields a polymer that is insoluble in water and can absorb less than 10 percent by weight water.

A "prepolymer" refers to a polymer that contains ethylenically unsaturated groups and can be polymerized actinically or thermally to form a polymer having a molecular weight larger than the starting prepolymer.

A "polymer" means a material formed by polymerizing/crosslinking one or more vinylic monomers, crosslinkers and/or prepolymers.

"Molecular weight" of a polymeric material (including monomeric or macromeric materials), as used herein, refers to the number-average molecular weight unless otherwise specifically noted or unless testing conditions indicate otherwise.

A "crosslinker" refers to a compound having at least two ethylenically-unsaturated groups. A "crosslinking agent" refers to a compound which belongs to a subclass of crosslinkers and comprises at least two ethylenically unsaturated groups and has a molecular weight of 700 Daltons or less.

A "polysiloxane vinylic monomer" refers to a vinylic monomer containing one sole ethylenically unsaturated group and one sole polysiloxane segment.

A "chain-extended polysiloxane vinylic monomer" refers to a compound which comprises one sole ethylenically unsaturated group and at least two polysiloxane segments separated by a linkage.

A "polysiloxane crosslinker" refers to a compound having at least two ethylenically unsaturated groups and one sole polysiloxane segment.

A "chain-extended polysiloxane crosslinker" refers to a linear polysiloxane compound which comprises at least two ethylenically unsaturated groups and at least two polysiloxane segments separated by a linkage.

The term "fluid" as used herein indicates that a material is capable of flowing like a liquid.

A free radical initiator can be either a photoinitiator or a thermal initiator. A "photoinitiator" refers to a chemical that initiates free radical crosslinking/polymerizing reaction by the use of light. Suitable photoinitiators include, without limitation, benzoin methyl ether, diethoxyacetophenone, a benzoylphosphine oxide, 1-hydroxycyclohexyl phenyl ketone, Darocure® types of photoinitiators, and Irgacure® types of photoinitiators, preferably Darocure® 1173, and Irgacure® 2959. Examples of benzoylphosphine oxide initiators include 2,4,6-trimethylbenzoyldiphenylophosphine oxide (TPO); bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a prepolymer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

A "thermal initiator" refers to a chemical that initiates radical crosslinking/polymerizing reaction by the use of heat energy. Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator is 2,2'-azobis(isobutyronitrile) (AIBN).

A "polymerizable UV-absorbing agent" refers to a compound comprising an ethylenically-unsaturated group and a UV-absorbing moiety which can absorb or screen out UV radiation in the range from 200 nm to 400 nm as understood by a person skilled in the art.

A "bulkyl vinylic monomer" refers to a vinylic monomer having a bulky substitute group. Preferred bulky vinylic monomers include without limitation N-[tris(trimethylsiloxy)silylpropyl]-(meth)acrylamide; N—[tris(dimethylpropylsiloxy)-silylpropyl](meth)acrylamide; N—[tris(dimethyl-phenylsiloxy)-silylpropyl](meth)acrylamide; N—[tris(dimethylethylsiloxy)silylpropyl](meth)acrylamide; N-(2-hydroxy-3-(3-(bis(trimethylsilyloxy)methylsilyl)propyloxy)propyl)-2-methyl acrylamide; N-(2-hydroxy-3-(3-(bis(trimethylsilyloxy)methylsilyl)propyloxy)propyl) acrylamide; N,N-bis[2-hydroxy-3-(3-(bis(trimethylsilyloxy)methylsilyl)propyloxy)propyl]-2-methyl acrylamide; N,N-bis[2-hydroxy-3-(3-(bis(trimethylsilyloxy)methylsilyl)propyloxy)propyl]acrylamide; N-(2-hydroxy-3-(3-(tris(trimethylsilyloxy)silyl)propyloxy)propyl)-2-methyl acrylamide; N-(2-hydroxy-3-(3-(tris(trimethylsilyloxy)silyl)propyloxy)propyl)acrylamide; N,N-bis[2-hydroxy-3-(3-(tris(trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethyl-silyl)propyloxy)propyl]acrylamide; N,N-bis[2-hydroxy-3-(3-(t-butyldimethylsilyl)propyloxy) propyl]-2-methyl acrylamide; N,N-bis[2-hydroxy-3-(3-(t-butyldimethylsilyl)propyloxy)propyl] acrylamide; 3-methacryloxy propylpentamethyldisiloxane; tris(trimethylsilyloxy)silylpropyl methacrylate (TRIS); (3-methacryloxy-2-hydroxypropyloxy)propylbis(trimethylsiloxy) methylsilane); (3-methacryloxy-2-hydroxypropyloxy)propyltris(trimethylsiloxy)silane; 3-methacryloxy-2-(2-hydroxyethoxy)-propyloxy)propylbis(trimethylsiloxy) methylsilane; N-2-methacryloxyethyl-O-(methyl-bis-trimethylsiloxy-3-propyl)silyl carbamate; 3-(trimethylsilyl)propylvinyl carbonate; 3-(vinyloxycarbonylthio)propyl-tris (trimethyl-siloxy)silane; 3-[tris(trimethylsiloxy)silyl] propylvinyl carbamate; 3-[tris(trimethylsiloxy)silyl]propyl allyl carbamate; 3-[tris(trimethylsiloxy)silyl]propyl vinyl carbonate; t-butyldimethyl-siloxyethyl vinyl carbonate; trimethylsilylethyl vinyl carbonate; trimethylsilylmethyl vinyl carbonate; t-butyl(meth)acrylate, cyclohexylacrylate, isobornyl methacrylate, a polysiloxane-containing vinylic monomer (having 3 to 8 silicone atoms), and combinations thereof.

As used herein, the term "ethylenically functionalized" in reference to a polysiloxane or a compound is intended to describe that one or more ethylenically groups have been covalently attached to the polysiloxane or the compound through its terminal (or pendant) reactive functional group(s) according to a coupling reaction, by using an ethylenically functionalizing vinylic monomer.

An "ethylenically functionalizing vinylic monomer" refers to a vinylic monomer having one reactive functional group capable of participating in a coupling (or crosslinking) reaction known to a person skilled in the art.

A "coupling reaction" is intended to describe any reaction between a pair of matching functional groups in the presence or absence of a coupling agent to form covalent bonds or linkages under various reaction conditions well known to a person skilled in the art, such as, for example, oxidation-reduction conditions, dehydration condensation conditions, addition conditions, substitution (or displacement) conditions, Diels-Alder reaction conditions, cationic crosslinking conditions, ring-opening conditions, epoxy hardening conditions, and combinations thereof. Non-limiting examples of coupling reactions under various reaction conditions between a pair of matching co-reactive functional groups selected from the group preferably consisting of amino group (—NHR' as defined above), hydroxyl group, carboxylic acid group, acid halide groups (—COX, X=Cl, Br, or I), acid anhydrate group, aldehyde group, azlactone group, isocyanate group, epoxy group, aziridine group, thiol group, and amide groups ($CONH_2$), are given below for illustrative purposes. A carboxylic acid group reacts with an amino group —NHR' in the presence of a coupling agent carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) to form an amide linkage; a carboxylic acid group reacts with an isocyanate group under heating to form an amide linkage; a carboxyl group reacts with an epoxy or aziridine group to form an ester bond; a carboxyl group reacts with a halide group (—Cl, —Br or —I) to form an ester bond; an amino group reacts with aldehyde group to form a Schiff base which may further be reduced; an amino group —NHR' reacts with an acid chloride or bromide group or with an acid anhydride group to form an amide linkage (—CO—NR'—); an amino group —NHR' reacts with an isocyanate group to form a urea linkage (—NR'—C(O)—NH—); an amino group NHR' reacts with an epoxy or aziridine group to form an amine bond (C—NR'—); an amino group reacts (ring-opening) with an azlactone group to form a linkage (—C(O)NH—$CR_1R_2$—$(CH_2)_r$—C(O)—NR'—); an amino group reacts with a halide group (—Cl, —Br or —I) to form an amine bond; a hydroxyl reacts with an isocyanate to form a urethane linkage; a hydroxyl reacts with an epoxy or aziridine or a halide group (—Cl, —Br or —I) to form an ether linkage (—O—); a hydroxyl reacts with an acid chloride or bromide group or with an acid anhydride group to form an ester linkage; an hydroxyl group reacts with an azlactone group in the presence of a catalyst to form a linkage (—C(O)NH—$CR_1R_2$—$(CH_2)_r$—C(O)—O—); a thiol group (—SH) reacts with an isocyanate to form a thiocarbamate linkage (—N—C(O)—S—); a thiol group reacts with an epoxy or aziridine to form a thioether linkage (—S—); a thiol group reacts with an acid chloride or bromide group or with an acid anhydride group to form a thiolester linkage; a thiol group reacts with an azlactone group in the presence of a catalyst to form a linkage (—C(O)NH-alkylene-C(O)—S—); a thiol group reacts with a vinyl group based on thiol-ene reaction under thiol-ene reaction conditions to form a thioether linakge (—S—); and a thiol group reacts with an acryloyl or methacryloyl group based on Michael Addition under appropriate reaction conditions to form a thioether linkage.

It is also understood that coupling agents with two reactive functional groups may be used in the coupling reactions. A coupling agent having two reactive functional groups can be a diisocyanate, a di-acid halide, a di-carboxylic acid compound, a di-acid halide compound, a di-azlactone compound, a di-epoxy compound, a diamine, or a diol. A person skilled in the art knows well to select a coupling reaction (e.g., anyone described above in this application) and conditions thereof to prepare a polysiloxane terminated with one or more ethylenically unsaturated groups. For example, a diisocyanate, di-acid halide, di-carboxylic acid, di-azlactone, di-epoxy compound can be used in the coupling of two hydroxyl, two amino groups, two carboxyl groups, two epoxy groups, or combination thereof; a diamine or dihydroxyl compound can be used in the coupling of two isocyanate, epoxy, aziridine, carboxylic acid, acid halide or azlactone groups or combinations thereof.

Any suitable $C_4$-$C_{24}$ diisocyanates can be used in the invention. Examples of preferred diisocyanates include without limitation isophorone diisocyanate, hexamethyl-1,6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyantomethyl)cyclohexane, cyclohexane diisocyanate, and combinations thereof.

Any suitable diamines can be used in the invention. An organic diamine can be a linear or branched $C_2$-$C_{24}$ aliphatic diamine, a $C_5$-$C_{24}$ cycloaliphatic or aliphatic-cycloaliphatic diamine, or a $C_6$-$C_{24}$ aromatic or alkyl-aromatic diamine. A preferred organic diamine is N,N'-bis(hydroxyethyl)ethylenediamine, N,N'-dimethylethylenediamine, ethylenediamine, N,N'-dimethyl-1,3-propanediamine, N,N'-diethyl-1,3-propanediamine, propane-1,3-diamine, butane-1,4-diamine, pentane-1,5-diamine, hexamethylenediamine, and isophorone diamine.

Any suitable diacid halides can be used in the invention. Examples of preferred diacid halide include without limitations fumaryl chloride, suberoyl chloride, succinyl chloride, phthaloyl chloride, isophthaloyl chloride, terephthaloyl chloride, sebacoyl chloride, adipoyl chloride, trimethyladipoyl chloride, azelaoyl chloride, dodecanedioic acid chloride, succinic chloride, glutaric chloride, oxalyl chloride, dimer acid chloride, and combinations thereof.

Any suitable di-epoxy compounds can be used in the invention. Examples of preferred di-epoxy compounds are neopentyl glycol diglycidyl ether, 1,4-butanediol diglycidyl ether, 1,6-hexanediol diglycidyl ether, glycerol diglycidyl ether, ethylene glycol diglycidyl ether, diethylene glycol diglycidyl ether, polyethylene glycol diglycidyl ether, propylene glycol diglycidyl ether, dipropylene glycol diglycidyl ether, and combinations thereof. Such di-epoxy compounds are available commercially (e.g., those DENACOL series di-epoxy compounds from Nagase ChemteX Corporation).

Any suitable $C_2$-$C_{24}$ diols (i.e., compounds with two hydroxyl groups) can be used in the invention. Examples of preferred diols include without limitation ethylene glycol, diethylene glycol, triethylene glycol, tetraethylene glycol, polyethylene glycol, propylene glycol, 1,4-butanediol, various pentanediols, various hexanediols, various cyclohexanediols, and combination thereof.

Any suitable $C_3$-$C_{24}$ di-carboxylic acid compounds can be used in the invention. Examples of preferred di-carboxylic acid compounds include without limitation a linear or branched $C_3$-$C_{24}$ aliphatic dicarboxylic acid, a $C_5$-$C_{24}$ cycloaliphatic or aliphatic-cycloaliphatic dicarboxylic acid, a $C_6$-$C_{24}$ aromatic or araliphatic dicarboxylic acid, a dicarboxylic acid which contains amino or imido groups or N-heterocyclic rings, and combinations thereof. Examples of suitable aliphatic dicarboxylic acids are: oxalic acid, malonic acid, succinic acid, glutaric acid, adipic acid, pimelic acid, suberic acid, azelaic acid, sebacic acid, undecanedioic acid, dodecanedioic acid, dimethylmalonic acid, octadecylsuccinic acid, trimethyladipic acid, and dimeric acids (dimerisation products of unsaturated aliphatic carboxylic acids, such as oleic acid). Examples of suitable cycloaliphatic dicarboxylic acids are: 1,3-cyclobutanedicarboxylic acid, 1,3-cyclopentanedicarboxylic acid, 1,3- and 1,4-cyclohexanedicarboxylic acid, 1,3- and 1,4-dicarboxylmethylcyclohexane, 4,4'-dicyclohexyldicarboxylic acid. Examples of suitable aromatic dicarboxylic acids are: terephthalic acid, isophthalic acid, o-phthalic acid, 1,3-, 1,4-, 2,6- or 2,7-naphthalenedicarboxylic acids, 4,4'-diphenyldicarboxylic acid, 4,4'-diphenylsulphone-dicarboxylic acid, 1,1,3-trimethyl-5-carboxyl-3-(p-carboxyphenyl)-indane, 4,4'-diphenyl ether-dicarboxylic acid, bis-p-(carboxylphenyl)-methane.

Any suitable $C_{10}$-$C_{24}$ di-azlactone compounds can be used in the invention. Examples of such diazlactone compounds are those described in U.S. Pat. No. 4,485,236 (herein incorporated by reference in its entirety).

The reactions conditions for the above described coupling reactions are taught in textbooks and are well known to a person skilled in the art.

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary, as illustrated in U.S. Pat. Nos. 6,800,225, 6,627,124, 7,384,590 and 7,387,759 (all of which are incorporated by reference in their entireties).

"Dye" means a substance that is soluble in a lens-forming fluid material and that is used to impart color. Dyes are typically translucent and absorb but do not scatter light.

A "pigment" means a powdered substance (particles) that is suspended in a lens-forming composition in which it is insoluble.

A "hydrophilic surface" in reference to a silicone hydrogel material or a contact lens means that the silicone hydrogel material or the contact lens has a surface hydrophilicity characterized by having an averaged water contact angle of about 100 degrees or less, preferably about 90 degrees or less, more preferably about 80 degrees or less, more preferably about 70 degrees or less.

An "average contact angle" refers to a water contact angle (measured by Sessile Drop), which is obtained by averaging measurements of at least 3 individual contact lenses.

An "antimicrobial agent", as used herein, refers to a chemical that is capable of decreasing or eliminating or inhibiting the growth of microorganisms such as that term is known in the art. Preferred examples of antimicrobial agent include without limitation silver salts, silver complexes, silver nanoparticles, silver-containing zeolites, and the likes "Silver nanoparticles" refer to particles which are made essentially of silver metal and have a size of less than 1 micrometer.

The term "soluble" in reference to a polysiloxane or prepolymer of the invention means that the polysiloxane or prepolymer can be dissolved in a solvent to an extent sufficient to form a solution of the prepolymer having a concentration of at least about 1% by weight at room temperature (about 22° C. to about 28° C.).

In accordance with the invention, the term "oxygen permeability" in reference to a contact lens means an estimated intrinsic oxygen permeability $Dk_c$ which is corrected for the surface resistance to oxygen flux caused by the boundary layer effect as measured according to the procedures described in Example 1. The intrinsic "oxygen permeability", Dk, of a material is the rate at which oxygen will pass through a material. Oxygen permeability is conventionally expressed in units of barrers, where "barrer" is defined as [($cm^3$ oxygen)(mm)/($cm^2$)(sec)(mm Hg)]×$10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as [($cm^3$ oxygen)/($cm^2$)(sec)(mm Hg)]×$10^{-9}$.

The "ion permeability" through a lens correlates with the Ionoflux Diffusion Coefficient. The Ionoflux Diffusion Coefficient, D (in units of [$mm^2$/min]), is determined by applying Fick's law as follows:

$$D=-n'/(A \times dc/dx)$$

where n'=rate of ion transport [mol/min]; A=area of lens exposed [$mm^2$]; dc=concentration difference [mol/L]; dx=thickness of lens [mm].

In general, the invention is directed to a class of actinically-crosslinkable chain-extended polysiloxane crosslinkers with two or more polysiloxane segments each pair of which is covalently linked together by a linker having at least one hydrophilic polymer chain that comprises at least about 60%, preferably at least about 70%, more preferably at least about 80%, even more preferably at least about 90%) by weight of one or more hydrophilic monomers. The invention is partly based on the discovery for preparing a crosslinkable linker with two reactive functional groups and at least one dangling hydrophilic polymeric chain. Such crosslinkable linker in turn can be used to prepare a chain extended polysiloxane crosslinker with defined structure.

There are several potential unique features associated with use of chain-extended polysiloxane crosslinkers of the invention in making silicone hydrogel contact lens. First, a chain-extended polysiloxane crosslinker of the invention in a silicone hydrogel contact lens formulation can be used to significantly improve the compatibility of polymerizable polysiloxane with other hydrophilic ingredients, such as, for example, a hydrophilic vinylic monomer and optionally a leachable polymeric wetting agent. It may be soluble in water, an ophthalmically compatible solvent (e.g., 1,2-propylene glycol, a polyethyleneglycol having a molecular weight of about 400 Daltons or less, or a combination thereof) or combination thereof and suitable for preparing a silicone hydrogel lens formulation. Second, a chain-extended polysiloxane crosslinker of the invention may be used to improve the surface wettability of a silicone hydrogel lens made from a lens forming material including such chain-extended polysiloxane crosslinker. It is known that a silicone hydrogel material typically has a surface or at least some areas of its surface, which is hydrophobic (non-wettable). Hydrophobic surface or surface areas will up-take lipids or proteins from the ocular environment and may adhere to the eye. Thus, a silicone hydrogel contact lens will generally require a surface modification which is typically carried out after cast-molding of the lens. It is believed that the presence of dangling hydrophilic polymer chains along polysiloxane (PDMS) chain may break up the size of hydrophobic domains on lens surface with accessible hydrophilic groups for moisture. It is also believed that when a solution of a chain-extended polysiloxane crosslinker of the invention is used as one of polymerizable components in a lens formulation for making silicone hydrogel contact lenses, the dangling hydrophilic polymer chains of the chain-extended polysiloxane crosslinker is preferably adsorbed at the interface between a mold for making contact lenses and the lens formulation. Where the dangling hydrophilic polymer chains is present in the crosslinker in an amount sufficient, an interfacial films, which is composed essentially of dangling hydrophilic polymer chains and has adequate thickness, can be formed at the mold-formulation interface prior to curing (polymerization) and subsequently preserved after curing. As such, one can make a silicone hydrogel contact lens with a hydrophilic interfacial film thereon without any post curing surface treatment. Third, a chain-extended polysiloxane crosslinker of the invention may be used to improve lens extraction efficiency, especially by water or an aqueous solution. Extraction of non-volatile residuals from lenses fabricated by monomer formulation is generally required to remove unpolymerized ingredients in the lens formulation. For silicone hydrogel lenses, the non-volatile extractables are usually performed using organic solvent due to the solubility of silicone containing extactables which are not fully soluble in aqueous solution. Presence of dangling hydrophilic polymer chains along the chain-extended polysiloxane chain may also enhance the solubility of extractables in aqueous solution in which the organic solvent can be minimized or even eliminated in extraction process.

The present invention, in one aspect, provides a linear chain-extended polysiloxane crosslinker which comprises: (1) two terminal ethylenically unsaturated groups, (2) at least two polysiloxane segments, and (3) at least one dangling hydrophilic polymer chain covalently attached to a divalent organic radical separating said at least two polysiloxane segments.

In accordance with the invention, the chain-extended polysiloxane crosslinker is preferably defined by formula (I)

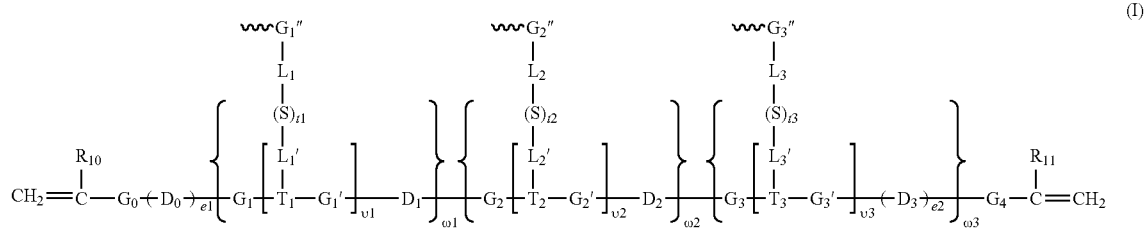

in which
$D_0, D_1, D_2$ and $D_3$ independently of one other are a divalent group of formula (II)

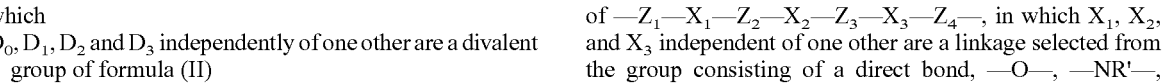

in which $G_5$ is as defined below, $A_1, A_2, A_3$, and $A_4$ independent of one other are a direct bond, a linear or branched $C_1$-$C_{10}$ alkylene divalent radical, —(CH(R'')CH$_2$O)$_{r1}$—CH(R'')CH$_2$— in which R'' is H or methyl and r1 is an integer of 1 to 20, or a $C_1$-$C_7$ alkyleneoxy $C_1$-$C_7$ alkylene divalent radical, $R_1, R_2, R_3, R_4, R_5, R_6, R_7, R_8, R_1', R_2', R_3', R_4', R_5', R_6', R_7'$, and $R_8'$ independently of one another are $C_1$-$C_8$-alkyl, $C_1$-$C_4$ alkyl- or $C_1$-$C_4$-alkoxy-substituted phenyl, fluoro($C_1$-$C_{18}$-alkyl), -alk-(OCH$_2$CH$_2$)$_n$—OR$_9$ in which alk is $C_1$-$C_6$-alkylene divalent radical, $R_9$ is $C_1$-$C_6$ alkyl and n is an integer from 1 to 20, a1 is an integer of 0 to 8, m1, m2, p1 and p2 independently of each other are an integer of from 0 to 150, (m1+p1) and (m2+p2) independent of each other are from 2 to 150;
e1, e2, t1, t2, and t3 independent of one other are an integer of 0 or 1;
υ1, υ2 and υ3 independent of one other are an integer of from 0 to 5 provided that (υ1+υ2+υ3)≥1;
ω1, ω2 and ω3 independent of one other are an integer of from 0 to 20 provided that (ω1+ω2+ω3) is an integer of 1 to 20;

$L_1, L_2$ and $L_3$ independent of one other is a direct bond,

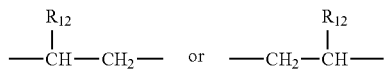

in which $R_{12}$ is hydrogen or $C_1$-$C_4$ alkyl;
$L_1', L_2'$ and $L_3'$ independent of one other is a direct bond or

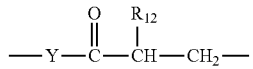

in which $R_{12}$ is as defined above, Y is —O— or —NR'— in which R' is hydrogen or $C_1$-$C_8$ alkyl, and Y is linked to $T_1, T_2$ or $T_3$;
$G_0, G_1, G_1', G_1'', G_2, G_2', G_2'', G_3, G_3', G_3'', G_4$, and $G_5$ independent of one other are a direct bond or a divalent radical of —$Z_1$—$X_1$—$Z_2$—$X_2$—$Z_3$—$X_3$—$Z_4$—, in which $X_1, X_2$, and $X_3$ independent of one other are a linkage selected from the group consisting of a direct bond, —O—, —NR'—,

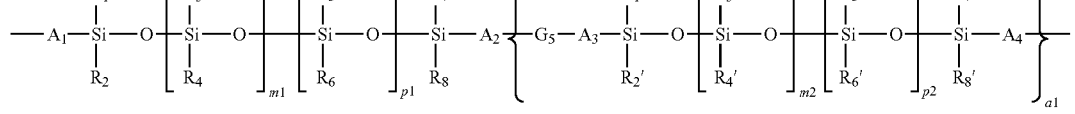

—C(O)—NR'—, —NR'—C(O)—, —O—C(O)—NH—, —NH—C(O)—O—, —NR'—C(O)—NH—, —NH—C(O)—NR'—, —S—, —C(O)—O—, —O—C(O)—, —NH—C(O)—NH—$Z_0$—NH—C(O)—NH—, —O—C(O)—NH—$Z_0$—NH—C(O)—O—, —O—C(O)—NH—$Z_0$—NH—C(O)—NH—, and —NH—C(O)—NH—$Z_0$—NH—C(O)—O—, $Z_0$ is a linear or branched $C_2$-$C_{12}$ alkylene divalent radical or a $C_5$-$C_{45}$ cycloaliphatic or aliphatic-cycloaliphatic divalent radical optionally containing therein one or more linkages of —O—, —NR'—, S and —C(O)—, R' is H or $C_1$-$C_8$ alkyl, $Z_1, Z_2, Z_3$, and $Z_4$ independent of one other are a direct bond, a linear or branched $C_1$-$C_{18}$ alkylene divalent radical optionally containing therein one or more linkages of —O—, —NR'—, —S— and —C(O)—, a $C_1$-$C_7$ alkyleneoxy $C_1$-$C_7$ alkylene divalent radical, a divalent radical of (CH(R'')CH$_2$O)$_{r1}$—CH(R'')CH$_2$ in which R'' and r1 are as defined above, an unsubstituted phenylene divalent radical, $C_1$-$C_4$ alkyl or $C_1$-$C_4$ alkoxy substituted phenylene divalent radical or $C_7$-$C_{12}$ arakylene divalent radical, a $C_5$-$C_{45}$ cycloaliphatic or aliphatic-cycloaliphatic divalent radical optionally containing therein one or more linkages of —O—, —NR'—, —S— and —C(O)—, a $C_6$-$C_{24}$ aromatic or araliphatic divalent radical, or combinations thereof;

$R_{10}$ and $R_{11}$ independent of each other are hydrogen or $C_1$-$C_4$ alkyl;

 is a linear or 3-arm (or Y-shape) hydrophilic polymer chain that comprises at least about 60%, preferably at least about 70%, more preferably at least about 80%, even more preferably at least about 90%) by weight of one or more hydrophilic monomeric units; and $T_1$, $T_2$ and $T_3$ independent of one other are a linear or branched $C_2$-$C_{24}$ aliphatic trivalent radical, a $C_5$-$C_{30}$ cycloaliphatic or aliphatic-cycloaliphatic trivalent radical, a $C_4$-$C_{30}$ aliphatic-heterocyclic trivalent radical including one or more oxygen or nitrogen atoms, or a $C_3$-$C_{24}$ aromatic or araliphatic trivalent radical.

In formula (II), $R_1$, $R_2$, $R_3$, $R_4$, $R_5$, $R_6$, $R_7$, and $R_8$ preferably are methyl.

In a preferred embodiment, t1, t2 and t3 in formula (I) are an integer of 1. Such a preferred chain-extended polysiloxane crosslinker can be obtained by a process including the steps of: (1) obtaining a bridging linker having a pendant (linear or 3-arm) hydrophilic polymer chain and two first reactive functional groups by (a) reacting a mercaptan having one sole thiol group and two first reactive functional groups (other than thiol groups) with a mono-ethylenically-functionalized hydrophilic polymer (i.e., a linear or 3-arm hydrophilic polymer having one sole terminal, ethylenically-unsaturated group), under Michael Addition or thiol-ene reaction conditions, (b) reacting mono-thiol terminated (linear or Y-shape) hydrophilic polymer with a vinylic monomer having two first reactive functional groups (other than ethylenically unsaturated groups), under Michael Addition or thiol-ene reaction conditions, or (c) polymerizing a mixture including a chain transfer agent (i.e., a mercaptan) having one sole thiol group and at least two first reactive functional groups, at least about 60%, preferably at least about 70%, more preferably at least about 80%, even more preferably at least about 90%) by weight of one or more hydrophilic vinylic monomers and from 0 to about 40% (preferably from 0 to about 30%, more preferably from 0 to about 20%, even more preferably from 0 to about 10%) by weight of one or more bulky vinylic monomers (any one described above); (2) reacting the bridging linker with at least one di-functional polysiloxane having one sole polysiloxane segment and two terminal second reactive functional groups, in the presence or absence of a coupling agent under coupling reaction conditions, to form an intermediary chain-extended polysiloxane polymer having two terminal first or second reactive functional groups, at least two polysiloxane segments, and at least one dangling hydrophilic polymer chain attached to an organic linkage linking a pair of adjacent polysiloxane segments; and (3) ethylenically functionalizing the intermediary chain-extended polysiloxane polymer by using an ethylenically functionalizing vinylic monomer having a third reactive functional group (other than ethylenically unsaturated group) capable of reacting with the first or second reactive functional groups in the presence or absence of a coupling agent to form a covalent linkage, thereby forming the chain-extended polysiloxane crosslinker of the invention (i.e., of formula (I)). Preferably, the first reactive functional group is selected from the group consisting of amino (—NHR' with R' as defined above), hydroxyl, carboxyl, and combinations thereof, and the second and third reactive functional groups independent of each other are selected from the group consisting of hydroxyl groups (—OH), amino groups (—NHR'), carboxyl groups (—COOH), isocyanate groups, epoxy groups, azlactone group, aziridine group, acid chloride, and combinations thereof.

In another preferred embodiment, in formula (I) t1, t2 and t3 are zero. Such a preferred chain-extended polysiloxane crosslinker can be obtained by a process including the steps of: (1) obtaining a bridging linker having a pendant (linear or 3-arm) hydrophilic polymer chain and two first reactive functional groups selected from the group consisting of amino, hydroxyl, carboxyl, isocyanate groups, and combinations thereof by (a) reacting a $C_2$-$C_{20}$ compound having three first reactive functional groups (which can be identical to or different from one other) with a (linear or 3-arm) hydrophilic polymer having one sole terminal second reactive functional group in the presence or absence of a coupling agent under coupling reaction conditions, or (b) reacting a $C_2$-$C_{20}$ compound having three first reactive functional groups (reactive with organic bromide) with a ATRP polymerization product of a polymerizing a mixture including an organic bromide as ATRP initiator, at least about 60% (preferably at least about 70%, more preferably at least about 80%, even more preferably at least about 90%) by weight of one or more hydrophilic vinylic monomers and from 0 to about 40% (preferably from 0 to about 30%, more preferably from 0 to about 20%, even more preferably from 0 to about 10%) by weight of one or more bulky vinylic monomers (any one described above); (2) reacting the bridging linker with at least one di-functional polysiloxane having one sole polysiloxane segment and two terminal third reactive functional groups, in the presence or absence of a coupling agent under coupling reaction conditions, to form an intermediary chain-extended polysiloxane polymer having two terminal first or third reactive functional groups, at least two polysiloxane segments, and at least one dangling hydrophilic polymer chain attached to an organic linkage linking a pair of adjacent polysiloxane segments; and (3) ethylenically functionalizing the intermediary chain-extended polysiloxane polymer by using an ethylenically functionalizing vinylic monomer having a fourth reactive functional group (other than ethylenically unsaturated group) capable of reacting with the first or third reactive functional groups in the presence or absence of a coupling agent to form a covalent linkage, thereby forming the chain-extended polysiloxane crosslinker of the invention (i.e., of formula (I)). Preferably, the second, third and fourth reactive functional groups independent of one another are selected from the group consisting of hydroxyl groups (—OH), amino groups (—NHR'), carboxyl groups (—COOH), epoxy groups, isocyanate groups, azlactone group, aziridine group, acid chloride, and combinations thereof.

The term "ATRP" refers to atom transfer radical polymerization which involves an organic halide (e.g., bromide) as ATRP initiator undergoing a reversible redox process catalyzed by a transition metal compound (e.g., cuprous bromide).

In a further preferred embodiment,  is a linear or 3-arm (or Y-shape) hydrophilic polymer chain that comprises at least about 60%, preferably at least about 70%, more preferably at least about 80%, even more preferably at least about 90%) by weight of one or more hydrophilic monomers selected from the group consisting of ethyleneoxide units, (meth)acrylamide units, $C_1$-$C_3$ alkyl(meth)acrylamide units, di-($C_1$-$C_3$ alkyl)(meth)acrylamide units, N-vinylpyrrole units, N-vinyl-2-pyrrolidone units, 2-vinyloxazoline units, 4-vinylpyridine units, mono-$C_1$-$C_4$ alkoxy, mono-(meth)acryloyl terminated polyethyleneglycol units having a molecular weight of 600 Daltons or less, di($C_1$-$C_3$ alkyl amino)($C_2$-$C_4$ alkyl)(meth)acrylate units, N—$C_1$-$C_4$ alkyl-3-methylene-2-pyrrolidone units, N—$C_1$-$C_4$ alkyl-5-methylene-2-pyrrolidone units, N-vinyl $C_1$-$C_6$ alkylamide units, N-vinyl-N—$C_1$-$C_6$ alkyl amide units, and combinations thereof. Preferably, the linear or 3-arm (or Y-shape) hydrophilic polymer chain comprises a bulky vinylic monomer (any one of those described above). The linear or 3-arm hydrophilic polymer chain has a molecular weight of about 10,000 Daltons or less, preferably about 8,000 Daltons or less, more preferably about 6,000 Dalton or less, even more preferably about 5,000 Dalton or less.

Examples of preferred hydrophilic vinylic monomers used in this aspect of the invention are N,N-dimethylacrylamide (DMA), N,N-dimethylmethacrylamide (DMMA), 3-acryloylamino-1-propanol, N-methyl-3-methylene-2-pyrrolidone, N-ethyl-3-methylene-2-pyrrolidone, N-methyl-5-methylene-2-pyrrolidone, N-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, dimethylaminoethyl methacrylate (DMAEMA), N-vinyl-2-pyrrolidone (NVP), a $C_1$-$C_4$-alkoxy polyethylene glycol(meth)acrylate having a weight average molecular weight of up to 1500, methacrylic acid, N-vinyl formamide, N-vinyl acetamide, N-vinyl isopropylamide, N-vinyl-N-methyl acetamide, N-vinyl caprolactam, and mixtures thereof.

Any bulkyl vinylic monomer described above can be used in this embodiment of the invention.

Any mercaptans having 2 to 24 carbon atoms and two reactive functional groups selected from the group consisting of amino (—NHR' with R' as defined above), hydroxyl, carboxyl, and combinations thereof can be used in the invention to prepare a bridging linker. Examples of such mercaptans include without limitation mercaptoglycerol, 2-Mercaptopyrimidine-4,6-diol; cysteine; 4-amino-5-mercapto-pentanoic acid, 2-mercapto-4-amino-6-hydroxypyrimidine, 2-mercapto-succinic acid, 3-mercapto-2-(methylamino)propanoic acid, 2-mercapto-4,5-dihydro-1h-imidazole-4,5-diol, 3-mercaptotyramine, mercaptopropanediol, 2-mercaptomethylglutaric acid, 3-mercapto-DL-valine hydrochloride, and combinations thereof.

Any vinylic monomer having two reactive functional groups selected from the group consisting of amino (—NHR' with R' as defined above), hydroxyl, carboxyl, and combinations thereof can be used in the invention to prepare a bridging linker having a pendant hydrophilic polymer chain. Examples of such vinylic monomers include without limitation N,N-2-(meth)acrylamidoglycolic acid, glycerol(meth)acrylate, 2-hydroxy-3-aminopropyl(meth)acrylate, 1-hydroxy-2-aminopropyl(meth)acrylate, 1-amino-2-hydroxypropyl(meth)acrylate, glutaconic acid, itaconic acid, citraconic acid, mesaconic acid, maleic acid, fumaric acid, and combinations thereof.

Any linear hydrophilic polymers having one sole thiol or ethylenically unsaturated group can be used in the invention to prepare a bridging linker having a pendant hydrophilic polymer chain. Exemplary hydrophilic polymers with one ethylenically-unsaturated group or thiol group include without limitation mono-ethylenically unsaturated group- or mono-thiol-terminated poly(ethylene glycol) (PEG); mono-ethylenically unsaturated group- or mono-thiol-terminated polyethyleneglycol/polypropyleneglycol (PEG/PPG) block copolymers; mono-ethylenically unsaturated group- or mono-thiol-terminated polymers comprising at least about 60% (preferably at least about 70%, more preferably at least about 80%, even more preferably at least about 90%) by weight of one or more hydrophilic vinylic monomers selected from the group consisting of N,N-dialkyl(meth)acrylamide, N-vinylpyrrolidone, N-methyl-N-vinylacetamide, N-vinylacetamide, N-vinyl formamide, N-vinyl isopropylamide, di-$C_1$-$C_4$ alkylamino-$C_2$-$C_4$ alkyl(meth)acrylate, (meth)acrylamide, a $C_1$-$C_4$-alkoxy polyethylene glycol (meth)acrylate having a weight average molecular weight of up to 200, N-methyl-3-methylene-2-pyrrolidone, 1-methyl-5-methylene-2-pyrrolidone, 5-methyl-3-methylene-2-pyrrolidone, or mixture thereof; and combinations thereof and from 0 to about 40% (preferably from 0 to about 30%, more preferably from 0 to about 20%, even more preferably from 0 to about 10%) by weight of one or more bulky vinylic monomers (any one of those described above).

Mono-ethylenically unsaturated group- or mono-thiol-terminated polyethyleneglycols (PEG's) are available from commercial sources. A monoethylenically unsaturated group-terminated hydrophilic polymer can be prepared by ethylenically functionalizing of a hydrophilic polymer having one sole reactive functional group selected from the group consisting of amino group, hydroxyl group, acid chloride group, carboxyl group, isocyanate group, anhydride, and epoxy group.

Various monofunctional terminated PEGs can be obtained from commercial sources, e.g., Shearwater Polymers, Inc. and Polymer Sources™. Preferred monofunctional-terminated PEGs are those PEGs with one amino, hydroxyl, acid chloride, or epoxy group at one terminus and a methoxy or ethoxy group at the other terminus. Various monofunctional polyvinylpyrrolidones (PVPs) with one terminal hydroxy, carboxyl or thiol group can be obtained from commercial sources, e.g., Polymer Sources™.

Monofunctional group-terminated linear hydrophilic polymers of one or more hydrophilic vinylic monomers free of any reactive functional group (other than ethylenically unsaturated group) can be prepared according to procedures similar to those described in U.S. Pat. No. 6,218,508, herein incorporated by reference in its entirety. For example, one or more hydrophilic vinylic monomers without functional group (i.e., primary amino group, hydroxyl group, isocyanate group, carboxyl group, or epoxy group), a small amount (i.e., about 40% or less, preferably about 30% or less, more preferably about 20% or less, even more preferably about 10% or less by weight, relative to the total amount of polymerizable components) of a blky vinylic monomer, and a chain transfer agent (e.g., 2-mercaptoethanol, 2-aminoethanethiol, 2-mercaptopropinic acid, thioglycolic acid, thiolactic acid, or other hydroxymercaptanes, aminomercaptans, or carboxyl-containing mercaptanes) are copolymerized (thermally or actinically) in the presence or absence of an initiator to obtain a monohydroxy-, moncarboxyl-, or monoamine-terminated hydrophilic polymer or copolymer. Generally, the molar ratio of chain transfer agent to that of one or more hydrophilic vinylic monomers is from about 1:5 to about 1.100. The molar ratio of chain transfer agent to the hydrophilic vinylic monomer without functional group is selected to obtain a polymer or copolymer with a molecular weight of from about 500 to about 20,000, preferably from about 750 to about 10,000 Daltons. Mono-epoxy-, mono-isocyanate-, or mono-acid chloride-terminated polymers or copolymers of one or more hydrophilic vinylic monomers can be prepared by covalently attaching epoxy, isocyanate, or acid chloride groups to the above-obtained monohydroxy- or monoamine-terminated polymers or copolymers of one or more hydrophilic vinylic monomers according to any known procedures. Use of monofunctional group-terminated hydrophilic polymers with higher molecular weight may ensure that the interfacial film on a silicone hydrogel material or lens made from a prepolymer of the invention has adequate thickness and coverage.

Alternatively, monofunctional group-terminated hydrophilic polymers can be prepared by polymerizing the one or more hydrophilic monomers (free of reactive functional group other than ethylenically unsaturated group) in the presence of a hydroxyl-, amine-, or carboxyl-containing free radical initiator at a molar ratio of intiator to the hydrophilic monomers of from about 1:30 to about 1:700. Examples of initiators with amine, hydroxyl, or carboxy group are azo initiators, such as, e.g., 2,2'-Azobis{2-[1-(2-hydroxyethyl)-2-imidazolin-2-yl]propane}dihydrochloride, 2,2'-Azobis{2-methyl-N-[1,1-bis(hydroxymethyl)-2-hydroxyethyl]propionamide, 2,2'-Azobis[2-methyl-N-(2-hydroxyethyl)propionamide], or 2,2'-Azobis{2-methyl-N-[2-(1-hydroxybutyl)]propionamide}, 2,2'-Azobis(2-methylpropionamide) dihydrochloride, 2,2'-Azobis[N-(2-carboxyethyl)-2-methylpropionamidine]tetrahydrate, or the likes.

In accordance with the invention, ethylenically functionalizing of a mono-functional group-terminated hydrophilic polymer can be carried out by covalently attaching ethylenically unsaturated groups to the functional groups (e.g., amine, hydroxyl, carboxyl, isocyanate, anhydride, and/or epoxy groups) of the mono-functional group terminated hydrophilic polymer by using an ethylenically functionalizing vinylic monomer. Any vinylic monomer having a hydroxy, amino, carboxyl, epoxy, aziridine, azlactone, acid-chloride, isocyanate group, which is coreactive with isocyanate, amine, hydroxyl, carboxy, anhydride, or epoxy group in the absence or presence of a coupling agent, can be used an ethylenically functionalizing vinylic monomer.

Examples of ethylenically-functionalizing vinylic monomers include without limitation $C_2$ to $C_6$ hydroxylalkyl(meth)acrylate, $C_2$ to $C_6$ hydroxyalkyl(meth)acrylamide, allylalcohol, allylamine, amino-$C_2$-$C_6$ alkyl(meth)acrylate, $C_1$-$C_6$ alkylamino-$C_2$-$C_6$ alkyl(meth)acrylate, vinylamine, amino-$C_2$-$C_6$ alkyl(meth)acrylamide, $C_1$-$C_6$ alkylamino-$C_2$-$C_6$ alkyl(meth)acrylamide, acrylic acid, $C_1$-$C_4$ alkylacrylic acid (e.g., methacrylic ethylacrylic acid, propylacrylic acid, butylacrylic acid), N—[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, aziridinyl $C_1$-$C_{12}$ alkyl(meth)acrylate (e.g., 2-(1-aziridinyl)ethyl(meth)acrylate, 3-(1-aziridinyl) propyl (meth)acrylate, 4-(1-aziridinyl) butyl(meth)acrylate, 6-(1-aziridinyl) hexyl(meth)acrylate, or 8-(1-aziridinyl)octyl (meth)acrylate), glycidyl(meth)acrylate, vinyl glycidyl ether, allyl glycidyl ether, (meth)acrylic acid halide groups (—COX, X=Cl, Br, or I), $C_1$ to $C_6$ isocyanatoalkyl(meth)acrylate, azlactone-containing vinylic monomers (e.g., 2-vinyl-4,4-dimethyl-1,3-oxazolin-5-one, 2-isopropenyl-4,4-dimethyl-1,3-oxazolin-5-one, 2-vinyl-4-methyl-4-ethyl-1,3-oxazolin-5-one, 2-isopropenyl-4-methyl-4-butyl-1,3-oxazolin-5-one, 2-vinyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4-tetramethylene-1,3-oxazolin-5-one, 2-vinyl-4,4-diethyl-1,3-oxazolin-5-one, 2-vinyl-4-methyl-4-nonyl-1,3-oxazolin-5-one, 2-isopropenyl-4-methyl-4-phenyl-1,3-oxazolin-5-one, 2-isopropenyl-4-methyl-4-benzyl-1,3-oxazolin-5-one, 2-vinyl-4,4-pentamethylene-1,3-oxazolin-5-one, and 2-vinyl-4,4-dimethyl-1,3-oxazolin-6-one, with 2-vinyl-4,4-dimethyl-1,3-oxazolin-5-one (VDMO) and 2-isopropenyl-4,4-dimethyl-1,3-oxazolin-5-one (IPDMO) as preferred azlactone-containing vinylic monomers), and combinations thereof.

Examples of $C_2$-$C_{20}$ compounds having three first reactive functional groups (which can be identical to or different from one other) include without limitation 3-amino-1,2-propanediol, 2-amino-1,3-propanediol, 2-amino-2-methylpropane-1,3-diol, α-aminoadipic acid, 2,3-dihydroxy-3-methylpentanoic acid, glyceric acid, 4-amino-2-hydroxybutanoic acid, 3-amino-2-hydroxypropionic acid, tyrosine, serine, threonine, lysine, aspartate, glutamate, 3-hydroxy-3-methylglutaric acid, malic acid, 2-hydroxyglutaric acid, glycerol, diglycerol, 1,1,1-trishydroxymethylethane, 1,1,1-trishydroxymethylpropane, 1,2,4-butanetriol, 1,2,6-hexanetriol, erythritol, pentaerythritol, diethylenetriamine, N-2'-aminoethyl-1,3-propylenediamine, N,N-bis(3-aminopropyl)-amine, N,N-bis(6-aminohexyl)amine, triethylenetetramine, the isocyanurate trimer of hexamethylene diisocyanate, 2,4,6-toluene triisocyanate, p, p', p"-triphenylmethane triisocyanate, and the trifunctional trimer (isocyanurate) of isophorone diisocyanate, trimesoyl chloride, cyclohexane-1,3,5-tricarbonyl chloride, trimer acid chloride, triglycidylisocyanurate (TGIC), trimethylopropane trimethacrylate, pentaerythritol tetramethacrylate, triallyl isocyanurate, triallyl cyanurate, aconitic acid, citric acid, 1,3,5-cyclohexanetricarboxylic acid, 1,3,5-trimethyl-1,3,5-cyclohexanetricarboxylic acid, 1,2,3 benzene tricarboxylic acid, and 1,2,4 benzene tricarboxylic acid. Preferably, a $C_2$-$C_{20}$ compound used for preparing a bridging linker having a pendant (linear or 3-arm) hydrophilic polymer chain and two first reactive functional groups (i.e., in formula (I) t1 and t2 is zero and $L_1$, $L_2$, $L_1'$ and $L_2'$ are direct bonds) is 3-amino-1,2-propanediol, 2-amino-1,3-propanediol, 2-amino-2-methylpropane-1,3-diol, α-aminoadipic acid, 2,3-dihydroxy-3-methylpentanoic acid, lysine, aspartate, or glutamate. A person skilled in the art understand well how to chose a coupling reaction based on selectivity and/or differential reactivity of a given functional group. For example, the amine group of 3-amino-1,2-propanediol can react with the sole carboxylic group of a monofunctionalized linear or 3-arm hydrophilic polymer in the presence of a carbodiimide (i.e., 1-ethyl-3-(3-dimethylaminopropyl)carbodiimide (EDC), N,N'-dicyclohexylcarbodiimide (DCC), 1-cylcohexyl-3-(2-morpholinoethyl)carbodiimide, diisopropyl carbodiimide) according to well-known carbodiimide-assisted coupling reaction, so as to form a bridging linker with one dangling linear or 3-arm hydrophilic polymer chain and two hydroxyl groups.

In accordance with the invention, the three arms of a monofunctional 3-arm hydrophilic polymer independent of each other are a linear hydrophilic polymer chain comprising at least about 60%, preferably at least about 70%, more preferably at least about 80%, even more preferably at least about 90% by weight of one or more hydrophilic monomers and they can be identical or different. Each arm is linked to a $C_2$-$C_{20}$ compound having three first reactive functional groups selected from the groups consisting of hydroxyl, amino, carboxyl, isocyanate groups, and combination thereof. A monofunctional 3-arm hydrophilic polymer can be prepared by reacting a first linear hydrophilic polymer having one sole terminal second reactive functional group with a $C_2$-$C_{20}$ compound having three first reactive functional groups to form a mono-di(first functional group) terminated linear hydrophilic polymer; reacting a second linear hydrophilic polymer having one sole third reactive functional group with the mono-di(first functional group) terminated linear hydrophilic polymer to form an intermediary hydrophilic polymer composed of the first and send linear hydrophilic polymers linked by a linkage with one first reactive functional group; and then reacting a third linear hydrophilic polymer having two terminal fourth reactive functional groups with the intermediary hydrophilic polymer to form a 3-arm hydrophilic polymer having one sole terminal fourth reactive functional group. Preferably, a $C_2$-$C_{20}$ compound having three first reactive functional groups for preparing a mono-functional terminated 3-arm hydrophilic polymer comprises three different reactive functional groups having different reactivities, for example, such as, 4-amino-2-hydroxybutanoic acid, 3-amino-2-hydroxypropionic acid, tyrosine, serine, or threonine.

Alternatively, a bridging linker having a pendant linear hydrophilic polymer chain and two first reactive functional groups (as described above) can be reacting sequentially with one mono-functional terminated linear hydrophilic polymer and with a linear hydrophilic polymer having two terminal functional groups under well known coupling reaction conditions, obtain a mono-functional terminated 3-arm hydrophilic polymer.

A mono-ethylenically unsaturated group terminated 3-arm hydrophilic polymer can be prepared by covalently attaching ethylenically unsaturated groups to the functional group (e.g., amine, hydroxyl, carboxyl, isocyanate, anhydride, and/or epoxy groups) of the mono-functional group terminated 3-arm hydrophilic polymer by using an ethylenically functionalizing vinylic monomer (as described above).

Any suitable di-functional polysiloxanes can be used to prepare an intermediary chain-extended polysiloxane polymer having two terminal reactive functional groups, at least two polysiloxane segments, and at least one dangling hydrophilic polymer chain attached to an organic linkage linking a pair of adjacent polysiloxane segments. Various polysiloxanes having two terminal functional groups selected from the group consisting of hydroxyl groups (—OH), amino groups (—NHR'), carboxyl groups (—COOH), epoxy groups, isocyanate groups, acid anhydride, and combinations thereof can be obtained from commercial suppliers (e.g., from Gelest, Inc, or Fluorochem). Otherwise, one skilled in the art will know how to prepare such difunctional group-terminated polysiloxanes according to procedures known in the art and described in Journal of Polymer Science—Chemistry, 33, 1773 (1995) (herein incorporated by reference in its entirety). Examples of commercially available di-functional polysiloxane include without limitation, di-epoxypropoxypropyl-terminated polysiloxane, di-hydroxyethoxypropyl-terminated polysiloxane, di-hydroxyl(polyethylenoxy)propyl-terminated polysiloxane, dicarboxydecyl-terminated polysiloxane, dicarboxypropyl-terminated polysiloxane, di-caprolactone terminated polysiloxane, di-N-ethylaminopropyl terminated polysiloxane, di-aminopropyl terminated polysiloxane, di-succinic acid anhydride terminated polysiloxane, and combinations thereof. A person skilled in the art will know well to select a di-functional polysiloxane and coupling reaction conditions in step (2).

It is understood that the molar equivalent ratio of the bridging linker having one pendant hydrophilic polymer chain to the difunctional terminated polysiloxane in coupling reaction mixture can determine whether resultant intermediary chain-extended polysiloxane polymer is capped with one of the two reactive functional group of the bridging linker or of the difunctional polysiloxane.

Where the molar equivalent ratio of a first bridging linker to a first di-functional terminated polysiloxane is about 2:1 in the coupling reaction mixture, the resultant first intermediary polysiloxane polymer has one polysiloxane segment and is capped with one of the two reactive functional group of the bridging linker. The first intermediary polymer then can be reacted with a second difunctional polysiloxane (which can be different from or the same as the first difunctional polysiloxane) at a molar equivalent ratio of 1:2 to form a second intermediary polysiloxane polymer having three polysiloxane segments and capped with one of the reactive functional groups of the second difunctional polysiloxane. Such procedures can be repeated to obtain an intermediary polymer having a desired number of polysiloxane segments.

Similarly, where the molar equivalent ratio of a first bridging linker to first difunctional terminated polysiloxane is about 1:2 in the coupling reaction mixture, the resultant first intermediary polysiloxane polymer has two polysiloxane segments and is capped with one of the two reactive functional group of the first difunctional polysiloxane. The resultant first intermediary chain-extended polysiloxane polymer then can be ethylenically functionalized to obtain a chain-extended polysiloxane crosslinker (i.e., step (3)) of the invention or reacted with a second bridging linker (which can be different from or the same as the first bridging linker) at a molar equivalent ratio of 1:2 to form a second intermediary polysiloxane polymer having the same two polysiloxane segments but capped with one of the reactive functional groups of the second bridging linker. The second intermediary polysiloxane can further be reacted with a second difunctional polysiloxane (which can be different from or the same as the first difunctional polysiloxanes) to form a third intermediary polysiloxane polymer having four polysiloxane segments and capped with one of the reactive functional groups of the second difunctional polysiloxane. Such procedures can be repeated to obtain an intermediary polymer having a desired number of polysiloxane segments.

It is understood that two or three bridging linkers can be covalently linked together, in a coupling reaction (any one described above), to form a new bridging linker having two or more pendant hydrophilic polymer chains (i.e., corresponding the formula (I) in which v1 and ω1 independent of each other are an integer of 2 or 3).

An intermediary chain-extended polysiloxane polymer obtained then can be ethylenically functionalized to obtain a chain-extended polysiloxane crosslinker of the invention, according to any ethylenically functionalizing procedures described above and using any ethylenically functionalizing vinylic monomer described above. Preferably, covalent linkages formed in the ethylenically functionalizing process are linkages free of ester linkages between one carbon-carbon double bond and one polydisiloxane segment. For example, where the terminal functional groups of an intermediary chain-extended polysiloxane polymer is amino or hydroxyl group, an azlactone-containing vinylic monomer or an isocyanate-containing (meth)acrylamide monomer (which can be for example the 1:1 reaction product of $C_2$-$C_4$ hydroxyalkyl (meth)acrylamide (e.g., hydroxyethyl(meth)acrylamide) with a hexamethyl-1,6-diisocyanate (or isophorene diisocyanate or any diisocyanate described above)) can be used as ethylenically functionalizing vinylic monomer; wherein the terminal functional groups of an intermediary chain-extended polysiloxane polymer are an amino group, a (meth)acrylic acid chloride can be as ethylenically functionalizing vinylic monomer; where the terminal functional groups of an intermediary chain-extended polysiloxane polymer are a 1,2- or 1,3-diol, acrylamidoacetaldehyde dimethylacetal (or methacrylamidoacetaldehyde dimethylacetal) can be used as ethylenically functionalizing vinylic monomer.

It should be understood that although in this aspect of the invention various embodiments including preferred embodiments of the invention may be separately described above, they can be combined and/or used together in any desirable fashion to arrive at different embodiments of a silicone hydrogel contact lenses of the invention.

In another aspect, the invention provides a soluble, amphiphilic prepolymer comprising: (1) crosslinking units derived from at least one chain-extended polysiloxane crosslinker having dangling hydrophilic polymer chains; (2) hydrophilic units derived from at least one hydrophilic vinylic monomer as well as at least two ethylenically unsaturated groups; (3) polymerizable units derived from a chain transfer agent and/or vinylic monomer having a reactive functional group and ethylenically unsaturated groups each covalently attached to the polymerizable units through the reactive functional group; (4) optionally hydrophobic units derived from a hydrophobic vinylic monomer; and (5) optionally UV-absorbing units derived from a polymerizable UV-absorbing agent, which is a further aspect of the invention. Such prepolymer of the invention is obtained by first polymerizing a polymerizable composition including (a) said at least one chain-extended polysiloxane crosslinker, (b) at least one hydrophilic vinylic monomer, (c) a chain transfer agent with or without a fourth reactive functional group (other than thiol group) and/or a vinylic monomer having a fifth reactive functional group (other than ethylenically unsaturated group), (d) optionally a hydrophobic vinylic monomer, and (e) optionally a polymerizable UV-absorbing agent, to form an intermediary copolymer and then by ethylenically functionalizing the intermediary copolymer with an ethylenically functionalizing vinylic monomer having a sixth reactive functional group capable of reacting with the first or second reactive functional group to form a linkage in a coupling reaction in the presence or absence of a coupling agent to form the prepolymer, wherein the fourth, fifth and sixth reactive functional groups independent of one another are selected from the group consisting of amino group NHR' with R' as defined above, hydroxyl group, carboxyl group, acid halide group, azlactone group, isocyanate group, epoxy group, aziridine group, and combination thereof. The methods for preparing such amphiphilic prepolymers are disclosed in commonly-owned U.S. Pat. Nos. 6,039,913, 6,043,328, 7,091,283, 7,268,189 and 7,238,750, 7,521,519; commonly-owned US patent application publication Nos. US 2008-0015315 A1, US 2008-0143958 A1, US 2008-0143003 A1, US 2008-0234457 A1, US 2008-0231798 A1, and commonly-owned U.S. patent application Ser. Nos. 12/313,546, 12/616,166 and 12/616,169; all of which are incorporated herein by references in their entireties.

Various embodiments of chain-extended polysiloxane crosslinkers, ethylenically functionalizing vinylic monomers, ethylenically functionalizing reactions, coupling reactions, and coupling agents are described above and can be used in this aspect of the invention.

Any suitable hydrophilic vinylic monomers can be used in this aspect of the invention. Suitable hydrophilic vinylic monomers are, without this being an exhaustive list, hydroxyl-substituted $C_2$-$C_4$ alkyl(meth)acrylates, hydroxyl-substituted $C_1$-$C_4$ alkyl vinyl ethers, $C_1$ to $C_3$ alkyl(meth)acrylamide, di-($C_1$-$C_3$ alkyl) (meth)acrylamide, N-vinylpyrrole, N-vinyl-2-pyrrolidone, 2-vinyloxazoline, 2-vinyl-4,4'-dialkyloxazolin-5-one, 2- and 4-vinylpyridine, olefinically unsaturated carboxylic acids having a total of 3 to 6 carbon atoms, amino-substituted $C_2$-$C_4$ alkyl- (where the term "amino" also includes quaternary ammonium), mono($C_1$-$C_3$ alkyl amino)($C_2$-$C_4$ alkyl) and di($C_1$-$C_3$ alkyl amino)($C_2$-$C_4$ alkyl) (meth)acrylates, allyl alcohol, N—$C_1$-$C_4$ alkyl-3-methylene-2-pyrrolidone, N—$C_1$-$C_4$ alkyl-5-methylene-2-pyrrolidone, N-vinyl $C_1$-$C_6$ alkylamide, N-vinyl-N—$C_1$-$C_6$ alkyl amide, and combinations thereof.

Examples of preferred hydrophilic vinylic monomers are N,N-dimethylacrylamide (DMA), N,N-dimethylmethacrylamide (DMMA), 2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethylmethacrylate (HEMA), 2-hydroxyethyl acrylate (HEA), hydroxypropyl acrylate, hydroxypropyl methacrylate (HPMA), trimethylammonium 2-hydroxy propylmethacrylate hydrochloride, aminopropyl methacrylate hydrochloride, dimethylaminoethyl methacrylate (DMAEMA), glycerol methacrylate (GMA), N-vinyl-2-pyrrolidone (NVP), allyl alcohol, vinylpyridine, a $C_1$-$C_4$-alkoxy polyethylene glycol(meth)acrylate having a weight average molecular weight of up to 1500, methacrylic acid, N-vinyl formamide, N-vinyl acetamide, N-vinyl isopropylamide, N-vinyl-N-methyl acetamide, N-vinyl caprolactam, and mixtures thereof. Among those preferred hydrophilic vinylic monomers, those free of any reactive functional group are particularly preferred for incorporating in the polymerizable composition for preparing the amphiphilic polysiloxane copolymer.

Any suitable hydrophobic vinylic monomers can be used in the preparation of a soluble, amphiphilic prepolymer of the invention. Examples of preferred hydrophobic vinylic monomers include methyl(meth)acrylate, ethyl(meth)acrylate, propyl(meth)acrylate, isopropyl(meth)acrylate, butyl(meth)acrylate, sec-butyl(meth)acrylate, isobutyl(meth)acrylate, t-butyl(meth)acrylate, cyclohexylacrylate, 2-ethylhexylacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate, a silicone-containing vinylic monomer, and mixtures thereof. Most preferably, the polymerizable composition comprises a bulky hydrophobic vinylic monomer, which can be any one of those bulky hydrophobic vinylic monomers described above.

It is believed that the presence of such bulky hydrophobic vinylic monomer in a prepolymer to be used as one of lens forming materials may be able to minimize or eliminate optical defects (permanent deformations) derived from handling during manufacturing in lenses made from the lens-forming materials. Such deformation or optical defect refers to permanent folding marks observed on the lens by a Contact Lens Optical Quality Analyzer (CLOQA) after the lens is folded manually as described in Example 1 of copending U.S. patent application Ser. No. 12/456,364 (herein incorporated by reference in its entirety). It is believed that when a bulky hydrophobic vinylic monomer is present, resultant lenses exhibit a 'healing' effect that eliminated the optical defects (i.e., the folding marks become transient and can disappear after a short time period, e.g., about 15 minutes or less).

Any polysiloxane-containing vinylic monomers and crosslinkers can be used in the invention. A polysiloxane-containing vinylic monomer or crosslinker can be obtained from commercial sources or be prepared according to any known procedures. Examples of preferred polysiloxane-containing vinylic monomers and crosslinkers include without limitation mono-(meth)acrylate-terminated polydimethylsiloxanes of various molecular weight (e.g., mono-3-methacryloxypropyl terminated, mono-butyl terminated polydimethylsiloxane or mono-(3-methacryloxy-2-hydroxypropyloxy)propyl terminated, mono-butyl terminated polydimethylsiloxane); mono-vinyl-terminated, mono-vinyl carbonate-terminated or mono-vinyl carbamate-terminated polydimethylsiloxanes of various molecular weight; di-(meth)acrylated polydimethylsiloxanes (or so called polysiloxane crosslinkers) of various molecular weight; di-vinyl carbonate-terminated polydimethylsiloxanes (polysiloxane crosslinkers); di-vinyl carbamate-terminated polydimethylsiloxane (polysiloxane crosslinkers); di-vinyl terminated polydimethylsiloxanes (polysiloxane crosslinkers); di-(meth)acrylamide-terminated polydimethylsiloxanes (polysiloxane crosslinkers); bis-3-methacryloxy-2-hydroxypropyloxypropyl polydimethylsiloxane (polysiloxane crosslinker); N,N,N',N'-tetrakis(3-methacryloxy-2-hydroxypropyl)-alpha,omega-bis-3-aminopropyl-polydimethylsiloxane (polysiloxane crosslinkers); polysiloxanylalkyl (meth)acrylic monomers; the reaction products of glycidyl methacrylate with amino-functional polydimethylsiloxanes; hydroxyl-containing polysiloxane vinylic monomers or crosslinkers; polysiloxane-containing crosslinkers disclosed in U.S. Pat. Nos. 4,136,250, 4,153,641, 4,182,822, 4,189,546, 4,343,927, 4,254,248, 4,259,467, 4,260,725, and 4,261,875, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5039,761, 5,346,946, 5,358,995, 5,387,632, 5,416,132, 5,451,617, 5,486,579, 5,962,548, 5,981,675, 6,039,913, and 6,762,264 (here incorporated by reference in their entireties); di- and tri-block macromers consisting of polydimethylsiloxane and polyalkyleneoxides (e.g., methacrylate end capped polyethyleneoxide-block-polydimethylsiloxane-block-polyethyleneoxide); and mixtures thereof.

Preferred polymerizable UV absorbing agents include without limitation 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl)benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxyethylphenyl)benzotriazole, 2-(2'-hydroxy-5'-methacryloxypropylphenyl)benzotriazole, 2-hydroxy-4-acryloxy alkoxy benzophenone, 2-hydroxy-4-methacryloxy alkoxy benzophenone, allyl-2-hydroxybenzophenone, 2-hydroxy-4-methacryloxy benzophenone. A polymerizable UV-absorbing agent is generally is present in the polymerizable composition for preparing a polysiloxane copolymer which is ethylenically functionalized in turn to obtain a polysiloxane prepolymer of the invention in an amount sufficient to render a contact lens, which is made from a lens forming material including the prepolymer and which absorbs at least about 80 percent of the UV light in the range of from about 280 nm to about 370 nm that impinges on the lens. A person skilled in the art will understand that the specific amount of UV-absorbing agent used in the polymerizable composition will depend on the molecular weight of the UV-absorbing agent and its extinction coefficient in the range from about 280 to about 370 nm. In accordance with the invention, the polymerizable composition comprises about 0.2% to about 5.0%, preferably about 0.3% to about 2.5%, more preferably about 0.5% to about 1.8%, by weight of a UV-absorbing agent.

A chain transfer agent (containing at least one thiol group) is used to control the molecular weight of the resultant intermediary copolymer. Where a chain transfer agent is free of any reactive functional group (other than thiol), a vinylic monomer having a reactive functional group (amine, hydroxyl, carboxyl, epoxy, isocyanate, azlactone, or aziridine group) is present in the polymerizable composition for preparing a prepolymer of the invention. Where a chain transfer has a reactive functional group such as amine, hydroxyl, carboxyl, epoxy, isocyanate, azlactone, or aziridine group, it can provide terminal or pendant functionality (amine, hydroxyl, carboxyl, epoxy, isocyanate, azlactone, or aziridine group) for subsequent ethylenical functionalization of the resultant intermediary copolymer. The vinylic monomer with a reactive functional group can provide another terminal or pendant hydroxyl, carboxyl or amino functionality to the resultant intermediary copolymer.

Generally, the molar ratio of chain transfer agent to that of one or more hydrophilic vinylic monomers is from about 1:5 to about 1:100, whereas the molar ratio of chain transfer agent to the vinylic monomer with a reactive functional group is 1:1. The molar ratio of chain transfer agent to the hydrophilic vinylic monomer without a reactive functional group (e.g., DMA, NVP) is selected to obtain a polymer or copolymer with a molecular weight of preferably from about 500 to about 20,000, more preferably from about 750 to about 10,000 Daltons.

The polymerizable composition for preparing an intermediary copolymer can be a melt, a solventless liquid in which all necessary components are blended together, or a solution in which all necessary component is dissolved in an inert solvent (i.e., should not interfer with the reaction between the reactants in the mixture), such as water, an organic solvent, or mixture thereof, as known to a person skilled in the art.

Example of suitable solvents includes without limitation, water, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimethyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methylpyrrolidinone, and mixtures thereof.

The copolymerization of a polymerizable composition for preparing an intermediary copolymer may be induced photochemically or preferably thermally. Suitable thermal polymerization initiators are known to the skilled artisan and comprise, for example peroxides, hydroperoxides, azo-bis (alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis(isobutyronitrile) (AIBN), 1,1-azodiisobutyramidine, 1,1'-azo-bis(1-cyclohexanecarbonitrile), 2,2'-azo-bis(2,4-dimethylvaleronitrile) and the like. The polymerization is carried out conveniently in an above-mentioned solvent at elevated temperature, for example at a temperature of from 25 to 100° C. and preferably 40 to 80° C. The reaction time may vary within wide limits, but is conveniently, for example, from 1 to 24 hours or preferably from 2 to 12 hours. It is advantageous to previously degas the components and solvents used in the polymerization reaction and to carry out said copolymerization reaction under an inert atmosphere, for example under a nitrogen or argon atmosphere. Copolymerization can yield optical clear well-defined copolymers which may be worked up in conventional manner using for example extraction, precipitation, ultrafiltration and the like techniques.

Preferably, an intermediary copolymer comprises: from about 15% to about 70% by weight, preferably from about 25% to about 60%, of crosslinking units derived from at least one chain-extended polysiloxane crosslinker having dangling hydrophilic polymer chains of the invention; from about 10% to about 60%, preferably from about 15% to 45% by weight, of hydrophilic units derived from one or more hydrophilic monomers; from 0 to about 30%, preferably from about 5% to about 25% of bulky hydrophobic units derived from one or more bulky hydrophobic vinylic monomers; and from 0 to about 5%, from about 0.2% to about 4%, preferably about 0.5% to about 2.5%, of a polymerizable UV-absorbing agent. All of the percentages above are weight percents based on the total weight of all polymerizable components including those not listed above.

A chain-extended polysiloxane crosslinker of the invention and a soluble amphiphilic prepolymer of the invention can find particular use in preparing silicone hydrogen ophthalmic lenses, in particular contact lenses.

It should be understood that although in this aspect of the invention various embodiments including preferred embodiments of the invention may be separately described above, they can be combined and/or used together in any desirable fashion to arrive at different embodiments of a silicone hydrogel contact lenses of the invention. All of the various embodiments described above for the previous aspect of the invention can be used alone or in combination in any desirable fashion in this aspect of the invention.

In a further aspect, the invention provides a soft contact lens. The soft contact lens of the invention comprises: a silicone hydrogel material that is obtained by curing a lens-forming material in a mold, wherein the lens-forming material comprises chain-extended polysiloxane crosslinker or a soluble amphiphilic prepolymer of the invention (as described above in detail) and one or more components selected from the group consisting of a hydrophilic vinylic monomer, a hydrophobic vinylic monomer, a crosslinking agent having a molecular weight of less than 700 Daltons, a polymerizable UV-absorbing agent, a visibility tinting agent (e.g., dyes, pigments, or mixtures thereof), antimicrobial agents (e.g., preferably silver nanoparticles), a bioactive agent, leachable lubricants, leachable tear-stabilizing agents, and mixtures thereof.

In accordance with the invention, a lens-forming material is a fluid composition, which can be a solution or a melt at a temperature from about 20° C. to about 85° C. Preferably, a lens-forming material is a solution of at least one prepolymer of the invention and other desirable components in water, or an organic solvent, or a mixture of water and one or more organic solvents.

Various embodiments of chain-extended polysiloxane crosslinkers, soluble amphiphilic prepolymers, hydrophilic vinylic monomers, hydrophobic vinylic monomers, solvents, crosslinking agents, polymerizable UV-absorbing agents, photoinitiators are described above and can be used in this aspect of the invention.

Examples of cross-linking agents include without limitation tetraethyleneglycol di-(meth)acrylate, triethyleneglycol di-(meth)acrylate, ethyleneglycol di-(meth)acrylate, diethyleneglycol di-(meth)acrylate, bisphenol A dimethacrylate, vinyl methacrylate, ethylenediamine di(meth)acrylamide, glycerol dimethacrylate, allyl(meth)acrylate, N,N'-methylenebis(meth)acrylamide, N,N'-ethylenebis(meth)acrylamide, N,N'-dihydroxyethylene bis(meth)acrylamide, 1,3-bis(methacrylamidopropyl)-1,1,3,3-tetrakis(trimethylsiloxy) disiloxane, 1,3-bis(N-(meth)acrylamidopropyl)-1,1,3,3-tetrakis-(trimethylsiloxy)disiloxane, 1,3-bis(methacrylamidobutyl)-1,1,3,3-tetrakis(trimethylsiloxy)-disiloxane, 1,3-bis(methacryloxyethylureidopropyl)-1,1,3,3-tetrakis(trimethylsiloxy)disiloxane, a product of diamine (preferably selected from the group consisting of N,N'-bis (hydroxyethyl)ethylenediamine, N,N'-dimethylethylenediamine, ethylenediamine, N,N'-dimethyl-1,3-propanediamine, N,N'-diethyl-1,3-propanediamine, propane-1,3-diamine, butane-1,4-diamine, pentane-1,5-diamine, hexamethylenediamine, isophorone diamine, and combinations thereof) and epoxy-containing vinylic monomer (prepferrably selected from the group consisting of glycidyl(meth) acrylate, vinyl glycidyl ether, allyl glycidyl ether, and combinations thereof), combinations thereof. A more preferred cross-linking agent to be used in the preparation of a prepolymer of the invention is tetra(ethyleneglycol)diacrylate, tri(ethyleneglycol)diacrylate, ethyleneglycol diacrylate, di(ethyleneglycol)diacrylate, glycerol dimethacrylate, allyl (meth)acrylate, N,N'-methylene bis(meth)acrylamide, N,N'-ethylene bis(meth)acrylamide, N,N'-dihydroxyethylene bis (meth)acrylamide, or combination thereof.

The bioactive agent incorporated in the polymeric matrix is any compound that can prevent a malady in the eye or reduce the symptoms of an eye malady. The bioactive agent can be a drug, an amino acid (e.g., taurine, glycine, etc.), a polypeptide, a protein, a nucleic acid, or any combination thereof. Examples of drugs useful herein include, but are not limited to, rebamipide, ketotifen, olaptidine, cromoglycolate, cyclosporine, nedocromil, levocabastine, lodoxamide, ketotifen, or the pharmaceutically acceptable salt or ester thereof. Other examples of bioactive agents include 2-pyrrolidone-5-carboxylic acid (PCA), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Examples of leachable lubricants include without limitation mucin-like materials (e.g., polyglycolic acid) and non-crosslinkable hydrophilic polymers (i.e., without ethylenically unsaturated groups).

Any hydrophilic polymers or copolymers without any ethylenically unsaturated groups can be used as leachable lubricants. Preferred examples of non-crosslinkable hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methacrylamide, a copolymer of acrylamide or methacrylamide with one or more hydrophilic vinylic monomers, polyethylene oxide (i.e., polyethylene glycol (PEG)), a polyoxyethylene derivative, poly-N—N-dimethylacrylamide, polyacrylic acid, poly 2 ethyl oxazoline, heparin polysaccharides, polysaccharides, and mixtures thereof. The weight-average molecular weight $M_w$ of the non-crosslinkable hydrophilic polymer is preferably from 5,000 to 500,000, more preferably from 10,000 to 300,000, even more preferably from 20,000 to 100,000 Daltons.

Examples of leachable tear-stabilizing agents include, without limitation, phospholipids, monoglycerides, diglycerides, triglycerides, glycolipids, glyceroglycolipids, sphingolipids, sphingo-glycolipids, fatty alcohols, fatty acids, mineral oils, and mixtures thereof. Preferably, a tear stabilizing agent is a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, or a mixture thereof.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In a preferred embodiment, reusable molds are used and the lens-forming composition is cured (i.e., polymerized) actinically under a spatial limitation of actinic radiation to form a silicone hydrogel contact lens. Examples of preferred reusable molds are those disclosed in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties. Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc.

In accordance with the invention, the lens-forming composition can be introduced (dispensed) into a cavity formed by a mold according to any known methods.

After the lens-forming composition is dispensed into the mold, it is polymerized to produce a contact lens. Crosslinking may be initiated thermally or actinically, preferably by exposing the lens-forming composition in the mold to a spatial limitation of actinic radiation to crosslink the polymerizable components in the lens-forming composition.

Where the lens-forming composition comprises a polymerizable UV-absorbing agent (i.e., a UV-absorbing moiety-containing vinylic monomer), a benzoylphosphine oxide photoinitiator is preferably used as the photoinitiator in the invention. Preferred benzoylphosphine oxide photoinitiators include without limitation 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. It is understood that any photoinitiators other than benzoylphosphine oxide initiators can be used in the invention.

Opening of the mold so that the molded article can be removed from the mold may take place in a manner known per se.

The molded contact lens can be subject to lens extraction to remove unpolymerized polymerizable components. The extraction solvent can be any solvent known to a person skilled in the art. Examples of suitable extraction solvent are those described above. After extraction, lenses can be hydrated in water or an aqueous solution of a wetting agent (e.g., a hydrophilic polymer).

The molded contact lenses can further subject to further processes, such as, for example, surface treatment (for example, such as, plasma treatment, chemical treatments, the grafting of hydrophilic monomers or macromers onto the surface of a lens, Layer-by-layer coating, etc.); packaging in lens packages with a packaging solution which can contain about 0.005% to about 5% by weight of a wetting agent (e.g., a hydrophilic polymer described above) and/or a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization; and the like.

A contact lens of the invention has an oxygen permeability of preferably at least about 40 barrers, more preferably at least about 55 barrers, even more preferably at least about 70 barrers. In accordance with the invention, an oxygen permeability is an apparent (directly measured when testing a sample with a thickness of, e.g., about 100 microns) oxygen permeability according to procedures described in Examples.

A contact lens of the invention has an elastic modulus of from about 0.1 MPa to about 2.0 MPa, preferably from about 0.2 MPa to about 1.5 MPa, more preferably from about 0.3 MPa to about 1.2 MPa, even more preferably from about 0.4 MPa to about 1.0 MPa.

A contact lens of the invention further has an Ionoflux Diffusion Coefficient, D, of, preferably at least about $1.0 \times 10^{-5}$ mm$^2$/min, more preferably at least about $2.0 \times 10^{-5}$ mm$^2$/min, even more preferably at least about $6.0 \times 10^{-5}$ mm$^2$/min.

A contact lens of the invention further has a water content of preferably from about 15% to about 55%, more preferably from about 20% to about 38% by weight when fully hydrated. The water content of a silicone hydrogel contact lens can be measured according to Bulk Technique as disclosed in U.S. Pat. No. 5,849,811.

It should be understood that although in this aspect of the invention various embodiments including preferred embodiments of the invention may be separately described above, they can be combined and/or used together in any desirable fashion to arrive at different embodiments of a silicone hydrogel contact lenses of the invention. All of the various embodiments described above for the previous aspects of the invention can be used alone or in combination in any desirable fashion in this aspect of the invention.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together. Therefore, the spirit and scope of the appended claims should not be limited to the description of the preferred versions contained therein.

Example 1

Oxygen Permeability Measurements

The apparent oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H. D. Cavanagh Ed., Raven Press: New York 1988, pp 273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm$^3$/min., while a nitrogen stream is passed on the opposite side of the lens at a rate of about 10 to 20 cm$^3$/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The apparent oxygen permeability of the lens material, $Dk_{app}$, is determined from the following formula:

$$Dk_{app} = Jt/(P_{oxygen})$$

where
J=oxygen flux [microliters O$_2$/cm$^2$–minute]
$P_{oxygen}=(P_{measured}-P_{water}$ vapor$)=$(% O$_2$ in air stream) [mm Hg]=partial pressure of oxygen in the air stream
$P_{measured}$=barometric pressure (mm Hg)
$P_{water}$ vapor=0 mm Hg at 34° C. (in a dry cell) (mm Hg)
$P_{water}$ vapor=40 mm Hg at 34° C. (in a wet cell) (mm Hg)
t=average thickness of the lens over the exposed test area (mm)
$Dk_{app}$ is expressed in units of barrers.

The apparent oxygen transmissibility (Dk/t) of the material may be calculated by dividing the apparent oxygen permeability ($Dk_{app}$) by the average thickness (t) of the lens.

The above described measurements are not corrected for the so-called boundary layer effect which is attributable to the use of a water or saline bath on top of the contact lens during the oxygen flux measurement. The boundary layer effect causes the reported value for the apparent Dk ($Dk_{app}$) of a silicone hydrogel material to be lower than the actual intrinsic Dk value ($Dk_i$). Further, the relative impact of the boundary layer effect is greater for thinner lenses than with thicker lenses. The net effect is that the reported Dk appear to change as a function of lens thickness when it should remain constant.

The intrinsic Dk value of a lens can be estimated based on a Dk value corrected for the surface resistance to oxygen flux caused by the boundary layer effect as follows.

Measure the apparent oxygen permeability values (single point) of the reference lotrafilcon A (Focus® N&D® from CIBA VISION CORPORATION) or lotrafilcon B (AirOptix™ from CIBA VISION CORPORATION) lenses using the same equipment. The reference lenses are of similar optical power as the test lenses and are measured concurrently with the test lenses.

Measure the oxygen flux through a thickness series of lotrafilcon A or lotrafilcon B (reference) lenses using the same equipment according to the procedure for apparent Dk measurements described above, to obtain the intrinsic Dk value ($Dk_i$) of the reference lens. A thickness series should cover a thickness range of approximately 100 μm or more. Preferably, the range of reference lens thicknesses will bracket the test lens thicknesses. The $Dk_{app}$ of these reference lenses must be measured on the same equipment as the test lenses and should ideally be measured contemporaneously with the test lenses. The equipment setup and measurement parameters should be held constant throughout the experiment. The individual samples may be measured multiple times if desired.

Determine the residual oxygen resistance value, $R_r$, from the reference lens results using equation 1 in the calculations.

$$R_r = \frac{\sum\left(\frac{t_j}{Dk_{app}} - \frac{t_j}{Dk_i}\right)}{n} \quad (1)$$

In which t is the thickness of a reference lens under measurement, and n is the number of the reference lenses measured. Plot the residual oxygen resistance value, $R_r$ vs. t data and fit a curve of the form Y=a+bX where, for the jth lens, $Y_j=(\Delta P/J)_j$ and $X=t_j$. The residual oxygen resistance, $R_r$ is equal to a.

Use the residual oxygen resistance value determined above to calculate the correct oxygen permeability $Dk_c$ (estimated intrinsic Dk) for the test lenses based on Equation 2.

$$Dk_c = t/[(t/Dk_a) - R_r] \quad (2)$$

The estimated intrinsic Dk of the test lens can be used to calculate what the apparent Dk ($Dk_{a\_std}$) would have been for a standard thickness lens in the same test environment based on Equation 3.

$$Dk_{a\_std} = L_{std}/[(t_{std}/Dk_c) + R_{r\_std}] \quad (3)$$

Ion Permeability Measurements.

The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of $0.314 \times 10^{-3}$ mm$^2$/minute.

Water Contact Angle (WCA) Measurements.

Water contact angle (WCA) measurements are performed by the sessile drop method with a DSA 10 drop shape analysis system from Kruss GmbH, Germany with pure water (Fluka, surface tension 72.5 mN/m at 20° C.). For measurement purposes a contact lens is taken off the storage solution with tweezers and excess storage solution is removed by gentle shaking. The contact lens are placed on the male part of a lens mold and gently blotted with a dry and clean cloth. A water droplet (approximately 1 µl) is then dosed on the lens apex, and the change of the contact angle over time of this water droplet (WCA(t), circle fitting mode) is monitored. The WCA is calculated by the extrapolation of the graph WCA(t) to t=0.

UV-Absorbance.

Contact lenses are manually placed into a specially fabricated sample holder or the like which can maintain the shape of the lens as it would be when placing onto eye. This holder is then submerged into a 1 cm path-length quartz cell containing phosphate buffered saline (PBS, pH ~7.0-7.4) as the reference. A UV/visible spectrophotometer, such as, Varian Cary 3E UV-Visible Spectrophotometer with a LabSphere DRA-CA-302 beam splitter or the like, can be used in this measurement. Percent transmission spectra are collected at a wavelength range of 250-800 nm with % T values collected at 0.5 nm intervals. This data is transposed onto an Excel spreadsheet and used to determine if the lenses conform to Class 1 UV absorbance. UV absorbance is calculated using the following equations:

$$UVA \% \ T = \frac{\text{Average } \% \ T \text{ between } 380-316 \text{ nm}}{\text{Luminescence } \% \ T} \times 100$$

$$UVB \% \ T = \frac{\text{Average } \% \ T \text{ between } 280-315 \text{ nm}}{\text{Luminescence } \% \ T} \times 100$$

In which Luminescence % T is the average % transmission between 380 and 780.

Example 2

This example illustrates one general procedure to synthesize crosslinkers according to scheme 1 as shown below (in scheme 1 ▭ and ∿∿∿∿ represent a polydimethylsiloxane segment and a hydrophilic polymer chain (e.g., polyethyleneglycol, PEG) respectively). It should be understand that different procedures known to a person skilled in the art can be used in the preparation of a crosslinker of the invention.

Scheme 1

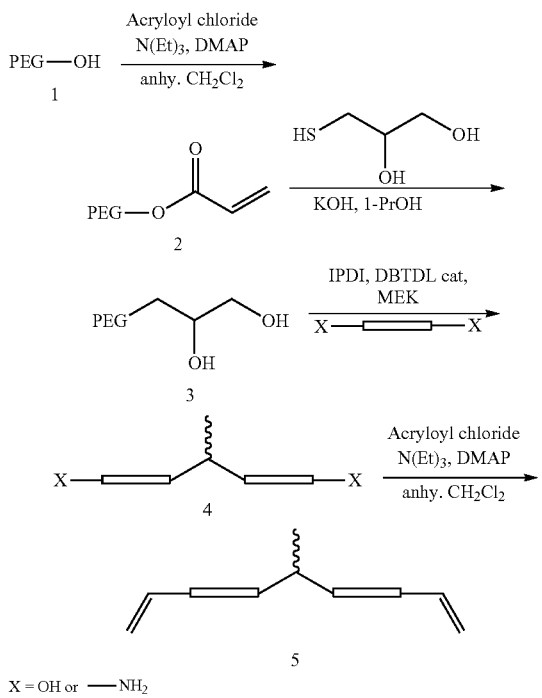

PEG monomethyl ether (Aldrich, 202509), acryloyl chloride (Aldrich, A24109), triethyl amine, N(Et)$_3$, (Acros, 219510500), 1-thio glycerol (Fluke, 88639), α,ω-di-aminopropyl terminated polydimethylsiloxane (Shin Etsu, KF-8012), and isophorone diisocyanate, IPDI (Aldrich, 317684) are purchased from vendors specified in the parenthesis.

Acrylation of PEG Monomethyl Ether (2)

256.67 g (0.128 mol) of PEG-monomethyl ether (1) is dissolved in 750 mL of anhydrous methylene chloride, and 37.7 g (0.373 mol) of triethyl amine is added to the reaction mixture. A freeze-pump-thaw process is repeated three times (freeze the reaction mixture in the flask in liquid nitrogen, evacuate under vacuum for 5 min, stop the vacuum and thaw the reaction mixture by dipping the flask in warm water), then nitrogen gas flow through the flask and catalytic amount of DMAP (4-dimethylamino pyridine) is added. The clear reaction mixture is cooled to 0° C. and kept under nitrogen gas. 58 g (0.64 mol) of acryloyl chloride is diluted with an equivalent amount of dry methylene chloride and then added to the reaction mixture by syringe in 1 hour. The reaction mixture turns yellow with acryloyl chloride addition. The reaction is then warmed to room temperature gradually and is stirred overnight. Following day, the reaction mixture is quenched with 200 mL of water and the solvent is removed on rotatory evaporator. The product, an off-white solid, is dissolved in 2

L of water, filtered and purified by water-based ultra-filtration. Colorless powder, 18 g (36%), is collected after freeze drying on the plate dryer.

Synthesis of Compound (3)

60.92 g (0.029 mol) 2 prepared above is dissolved in 600 mL of THF at 35° C. in a 1 L 3 neck flask and stirred under nitrogen. 7.48 g (0.069 mol) of 1-thio glycerol is added to the reaction mixture. After that 15 mL of 1N KOH solution in 1-propanol is added. Reaction mixture is stirred at 35° C. for 2-3 h and reaction completion is monitored by thiol titration. After reaction completion, reaction mixture is acidified by adding 1N HCl. 1 L of water is added to reaction mixture, and then solvent is removed under reduced pressure. Next, product is purified by ultra filtration and freeze dried. 45.7 g (68%) colorless solid is collected.

Synthesis of Compound (4)

5.02 g (2.28 mmol) of PEG-glycerol (3) and 1.22 g (5.53 mmol) of isophorone diisocyanate (IPDI) are dissolved in 40 mL of MEK in a 2 neck flask and flash with nitrogen for 15 min. 3 drops of dibutyltin dilaurate (DBTDL) catalyst is added to the mixture and stirred at 35° C. overnight under nitrogen atmosphere. Next day, 24.04 g (5.34 mmol) of KF-8012 is added to the reaction pot to react further to form difunctional hydrophilized PDMS cross-linker. The reaction is stirred overnight at 38° C. Next day, the reaction is stopped and solvent is removed under reduced pressure. Crude product, an off-white oily paste, is triturated in n-hexane, filtered and dried. 27.8 g (89%) off-white solid is collected.

Synthesis of Crosslinker (5)

22.00 g (1.913 mmol) 4 is acrylated as explained above for 2, only purified differently. Crude product in $CH_2Cl_2$ is extracted with water (2×200 mL). Organic layers are combined and dried over $MgSO_4$, filtered and solvent is removed reduced pressure. 19.09 g (96%) off-white paste is collected.

Analysis of Products

Products are analyzed by $^1H$ NMR, and GPC. GPC data shows that the molecular weight of diamino PDMS is doubled due to the formation of urea linkages with IPDI to form product 4 and MW of the acrylation product 5 stays the same.

Example 3

This example illustrates the synthesis of polydimethylsiloxane crosslinkers with using different hydrophilic and hydrophobic groups and molecular weights as starting materials to form many different structures. Resultant hydrophilized PDMS cross-linkers are included in formulations to achieve self-wettable lens surface with acceptable lens properties. A variety of cross-linkers are prepared from different combinations of hydrophiles, IPDI and PDMSs according to procedures described in Example 2 as shown in Scheme 2.

Scheme 2

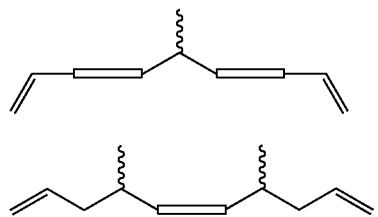

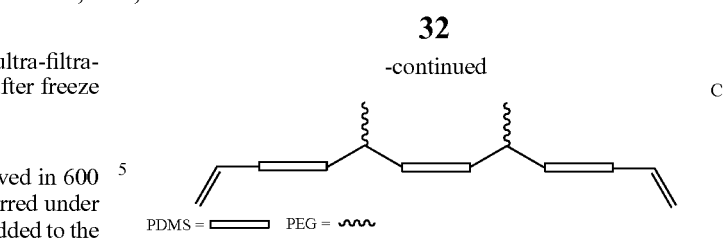

Michael addition between PEG-acrylate (2000 MW) and thioglycerol is carried out in 1-PrOH and colorless product is achieved with 100% conversion. Product is analyzed by $^1H$ NMR. PEG-thioglycerol (MW=2000) is reacted with IPDI and 3000 and/or 4500 MW PDMS-diamine/diol in MEK under $N_2$ atmosphere. Product is acrylated in $CH_2Cl_2$.

PDMS crosslinkers prepared above are formulated either alone (macromer) or in combinations with vinylic monomers to form two types of lens formulations (i.e., polymerizable compositions) as shown in Table 1.

TABLE 1

| Ingredients | Formulation Types | |
|---|---|---|
| (% by weight) | I | II |
| Cross linker | 6 | 31.5 |
| Tris acrylamide | | 20.5 |
| DMA | | 23 |
| Daracure 1173 | 0.1 | 1 |
| 1-propanol | 39 | 24 |

Tris acrylamide: N-[tris(trimethylsiloxy)silylpropyl] acrylamide

Contact lenses are produced by cast molding of one of the above-prepared lens formulations using one of double sided molding (DSM) or LIGHTSTREAM™ (LS) techniques.

DSM or LS lenses are fabricated from these formulations. Lenses are easily removed from molds, extracted in ethanol and are not subjected to post-curing surface treatment.

LS lenses are prepared by cast-molding from a lens formulation prepared as above in a reusable mold, similar to the mold shown in FIGS. 1-6 in U.S. Pat. Nos. 7,384,590 and 7,387,759 (FIGS. 1-6). The mold comprises a female mold half made of $CaF_2$ and a male mold half made of PMMA. The UV irradiation source is a Hamamatsu lamp with a 380 nm-cut-off filter at an intensity of about 4.6 mW/cm². The lens formulation in the mold is irradiated with UV irradiation for about 30 seconds. Cast-molded lenses are extracted with isopropanol (or methyl ethyl ketone, MEK), rinsed in water, hydrated in water, packaged/autoclaved in lens packages containing a phosphate-buffered saline.

DSM lenses are prepared as follows. Female portions of polypropylene lens molds are filled with about 75 microliters of a lens formulation prepared as above, and the molds are closed with the male portion of the polypropylene lens molds (base curve molds). Contact lenses are obtained by curing the closed molds for about 5 minutes with an UV irradiation source (Hamamatsu lamp with a 330 nm-cut-off filter at an intensity of about 16 mW/cm²). Cast-molded lenses are extracted with isopropanol or methyl ethyl ketone (MEK), rinsed in water, hydrated in water, packaged/autoclaved in lens packages containing a phosphate-buffered saline.

Photo-rheology is studied by using the Hamamatsu lamp with a stack of 330 nm and 388 nm long pass cutoff filters placed just before the sample. The intensity (about 4 mW/cm²) is measured by using an IL1700 detector using a SED005 sensor with a 297 nm cutoff filter from International light, the long pass filters are placed before curing the formulation. The results of photorheology study are reported shown in Table 2.

TABLE 2

| X-linker | Formulation No/MW PDMS | Formulation Type | Photorheology | | |
|---|---|---|---|---|---|
| | | | cure time (s) | G', KPa | WCA (degree)* |
| A | SB-1/4500 | I | 38 | 155 | 89 |
| A | SB-2/3000 | I | 30 | 275 | 81 |
| C | SB-3/3000 | I (50%) | 109 | 110 | 91 |
| C | SB-4/3000 | II | 162 | 100 | 112 |

*Measured by Sessile drop.

Uncoated lenses do not stick to each other or to the container (glass vial or polypropylene cup). They feel slippery and sink in water. Lenses are also evaluated by sessile drop contact angle measurements, shown in Table 2. Most lenses are clear, but slightly yellow and fragile.

Example 4

This example illustrates how to prepare a chain-extended PDMS crosslinker with pendant polyethyleneglycol (PEG) chains.

Intermediary Copolymer Synthesis

The step wise reaction is started by addition of 20.58 g (10.29 mmol) mono-amino terminated Jeffamine (polyethyleneglycol-NH$_2$, MW=2000 Daltons) solution in 40 mL THF to a chilled 10.00 g (10.29 mmol) Vestanat solution in 500 gTHF (tetrahydrofurane) by addition funnel in about 30 minutes. After stirring mixture at 0° C. for about 30 minutes, the reaction mixture is brought to room temperature and stirred for additional about 2 hours. A solution of 69.98 g (15.55 mmol) di-aminpropyl terminated polydimethylsiloxane (KF-8012, MW=4500 Daltons) in 40 mL of THF is prepared in another flask and cooled to 0° C. in ice bath. The Jefamine/Vestanat portion is added to the PDMS solution in ice bath by addition funnel in about 30 minutes. After stirring the mixture in ice bath for about 30 minutes, it is stirred at room temperature (RT) for about 2 more hours. 300 mL of isopropyl alcohol (IPA) is added to the reaction mixture and THF is removed under reduced pressure on rota-vap, after that 1000 mL of water is added slowly and lastly IPA is removed. Intermediary copolymer with two terminal amino groups and pendant PEG chains is obtained and used immediately in acrylation reaction.

Acrylation of Amino-Terminated Intermediary Copolymers

The acrylation reaction of amino-terminated intermediary copolymers is performed in an aqueous environment under basic conditions. The solvent exchanged copolymer (1000 mL) is charged to a cooled (0° C.) reactor which is equipped with stirrer shaft, thermometer, and aqueous pH probe. Reaction mixture is mixed at 300 rpm. In a separate glass beaker, required amount (which is determined based on the determined amino content of the intermediary copolymer) of sodium bicarbonate is dissolved in deionized water and slowly added to the reactor. Additional water may be required to ensure that pH probe is submerged into reaction solution. Metrohm automatic titrator and pH probe are connected. Reservoir containing 20% NaOH solution is inserted onto titrator and solution dispensing tube is placed into reactor. Once thermometer indicates that reaction solution temperature is at 0° C., titrator is set up to dispense 20% NaOH to the mixture until reaction pH reaches 9.5. Next, the required volume (which is determined based on the determined amino content of the intermediary copolymer) of acryloyl chloride is dispensed into Hamilton gas-tight syringe and extension tubing is attached to the syringe and placed into the reactor. Syringe should be placed inside the automatic dispenser module and programmed to add the total volume of acryloyl chloride at a constant rate over a 120 minute period. Automatic titrator dispensing of 20% NaOH solution is maintained during acryloyl chloride addition to maintain reaction pH at 9.5. Once acryloyl chloride addition is complete, temperature is maintained and reaction mixture is stirred for an addition 60 minutes. After additional mixing time, temperature is raised to 25° C. Once desired temperature is reached, NaOH reservoir is removed and reservoir containing 2N HCl is inserted. Dispensing tubing is placed inside reactor and titrator is programmed to dispense acid until the pH of the reaction is 7.0. Reaction mixture is mixed for an additional 30 minutes. Once reaction is complete; solution is drained out of reactor and filtered with medium fritted funnel to remove any particles. Purification is performed by ultrafiltration with 5K membrane. Ultra filtered material is freeze dried on lyophilizer.

Cross-linkers with pendant linear Jeffamine chain are prepared from Jeffamine 2000, Vestanat (isocyanurate, trimer, of isophorone diisocyanate), and PDMS (MW=4500 and 3000 Daltons) at different ratios of hydrophiles and hydrophobes, as listed in Table 3.

TABLE 3

| | M.W. of PDMS | Stoichiometric ratio: Vestanat:Jeffamine:PDMS | Structure |
|---|---|---|---|
| Crosslinker 1 | 4500 | 1:1:2 | 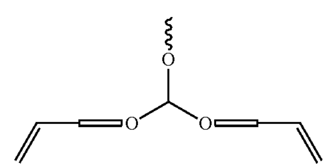 |
| Crosslinker 2 | 4500 | 2:2:3 | 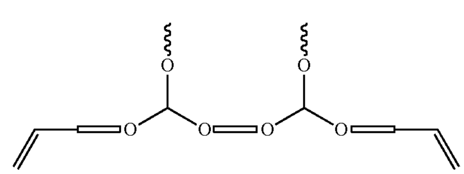 |

TABLE 3-continued

| | M.W. of PDMS | Stoichiometric ratio: Vestanat:Jeffamine:PDMS | Structure |
|---|---|---|---|
| Crosslinker 3 | 3000 | 2:2:3 | 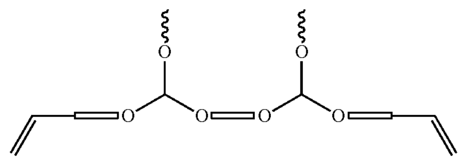 |
| Crosslinker 4 | 4500/3000 | 2:2:3 | 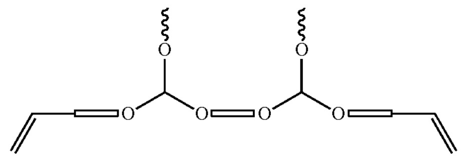 |

Example 5

Contact lenses are prepared by cast molding of a lens formulation including a crosslinker prepared in Example 4, according to the procedures described in Example 3 (formulation type I). The lens properties of lens formulations and contact lenses prepared therefrom are reported in Table 4.

TABLE 4

| Crosslinker | 1 | 1 | 2 | 3 | 4 |
|---|---|---|---|---|---|
| Solid content[1] | 60% | 75% | 75% | 75% | 70% |
| Photorheology: cure time (s)[2] | 11 | 7 | 6 | 7 | 6 |
| Photorheology: G' (KPa)[2] | 73 | 161 | 118 | 92 | 72 |
| WCA (Adv/Rec)[3] | 92 (92/13) | | 88 (86/12) | 91 (88/15) | 83 (79/16) |
| Modulus (MPa) | | | | 2.26 | 2.01 |
| Max. Elongation | | | | 119% | 153% |
| $Dk_c$ (barrer) | 183 | | 493 | 562 | 884 |
| Ion permeability[4] | No value | No value | 0 | 2.3 | No value |

[1]1-propanol is the solvent;
[2]Irradiation source: 4.0 mW/cm², with 297 nm cutoff filter;
[3]Water contact angle measured by Sessile drop method;
[4]Ion permeability related to Alsacon lens.

Five lens formulations are prepared by dissolving crosslinkers prepared in Example 4, N,N-dimethylacrylamide (DMA), N—[tris(trimethylsiloxy)silylpropyl]-acrylamide (TRIS-Am, from ShinEtsu #805001) in 1-propanol to have the compositions shown in Table 5. All formulations are clear.

TABLE 5

| Formulation No. | Crosslinker (No.) | DMA | TRIS-Am | Darocur 1173 |
|---|---|---|---|---|
| I | 31.8 (1) | 23.2 | 20.7 | 1.0 |
| II | 41.26 (1) | 20.18 | 17.90 | 0.86 |
| III | 48.37 (1) | 17.66 | 15.74 | 0.76 |
| IV | 48.37 (3) | 17.66 | 15.74 | 0.76 |
| V | 41.26 (4) | 20.18 | 17.90 | 0.86 |

The lens properties of lens formulations and contact lenses prepared therefrom are reported in Table 6. However, lenses become hazy after autoclave.

TABLE 6

| Formulation No. | I | II | III | IV | V |
|---|---|---|---|---|---|
| Photorheology: cure time (s)[1] | 14 | 12 | 14 | 11 | 13 |
| Photorheology: G' (KPa)[1] | 54 | 90 | 69 | 92 | 62 |
| WCA (Adv/Rec)[2] | 103 (106/14) | 107 (102/17) | 98 (90/12) | 100 (95/13) | 102 (95/15) |
| Modulus (MPa) | | 0.7 | 0.7 | 0.74 | 0.5 |
| Max. Elongation | | 221% | 223% | 184% | 280% |
| $Dk_c$ (barrer) | 128 | 161 | 154 | 118 | 123 |
| Ion permeability[3] | 25.2 | 18.0 | 21.6 | 23.7 | 28 |

[1]Irradiation source: 16.0 mW/cm², with 330 nm cutoff filter;
[2]Water contact angle measured by Sessile drop method;
[4]Ion permeability related to Alsacon lens.

Example 6

This example illustrates how to prepare a chain-extended PDMS crosslinker with pendant 3-arm hydrophilic polymer chains according to a step-wise reaction process.

Mono-Amino-Terminated Hydrophilic Polymer with 3 Arms of PEG

A mono-amino-terminated 3-arm hydrophilic polymer having the structure of

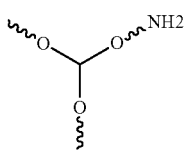

is prepared as follows. A solution of 30 g (28.41 mmol) Vestanat is prepared in 400 mL of THF and cooled to 0° C. Mono-amino terminated 113.64 g (56.82 mmol) Jeffamine M2070 is dissolved in 40 mL of THF and added to a stirring Vestanat solution by addition funnel in 30 minutes. Reaction temperature is maintained during the Jeffamine addition and for additional 1 hour. Reaction mixture is stirred additional 1 hour at room temperature. In another flask, diamine functional 56.80 g (28.40 mmol) Jeffamine ED2003 (polyethyleneglycol diamine, MW=2000 Daltons) solution is prepared in 40 mL of THF and cooled to 0° C. Jeffamine M2070/Vestanat reaction mixture is added to a solution of ED2003 by addition funnel in 30 minutes at 0° C. Reaction mixture is stirred for 1 h after addition at 0° C. and then at room temperature for additional 1 h. After solvent exchange process as explained earlier, material is purified by ultrafiltration with 3K membrane and freeze dried.

Mono-Amino-Terminated Polymer with One Arm of PVP and Two Arms of PEG

A mono-amino-terminated 3-arm hydrophilic polymer having the structure of

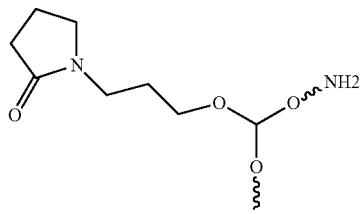

is prepared according to the procedures described above for preparing 3-PEG arm polymer. Additionally after water ultra-filtration, material is re-purified by using ceramic ultra filtration (5K) to remove nonfunctional (dimerized) branched Jeffamine/pyrrolidone.

Intermediary Copolymer Synthesis

Intermediary copolymer having PDMS segments and pendant 3-arm hydrophilic polymer chains are prepared from the mono-amino terminated 3-arm polymers prepared above according to the procedures described in Example 4. Di-amino-terminated PDMS (M.W. 4500 Daltons) is used in the preparation.

Acrylation of Intermediary Copolymers

Acrylation of di-amino-terminated intermediary copolymers are carried out according to the procedures described in Example 4.

Example 7

Two crosslinkers (crosslinkers 5 and 6) are prepared according to the procedures described in Example 6 and have the compositions and structures shown in Table 7.

The prepared crosslinkers are formulated alone and with monomers (combinations of DMA, TRIS, PEG acrylate and MBA) with Darocure 1173 in 1-propanol. The formulation compositions, photorheology and lens property data are shown in Table 8. Cross-linkers with branched hydrophiles show enhanced wettability compare to other hydrophiles, formulation VI showed sessile contact angle of 71° with acceptable lens properties. Both monomer and alone formulations of these cross-linkers have very high viscosity (10000-42000 mPasec) in the region of 60-75% solid content.

TABLE 8

| Ingredients | Formulation Types | | | |
|---|---|---|---|---|
| (% by weight) | VI | VII | IIX | IX |
| Cross linker 5 | 6.3 | | 5.8 | |
| Cross linker 6 | | 6.0 | | 5.6 |
| Tris acrylamide | | | 0.9 | 0.9 |
| DMA | | | 0.9 | |
| Daracure 1173 | 0.1 | 0.1 | 0.1 | 0.1 |
| 1-propanol | 3.6 | 3.9 | 2.3 | 34 |
| Photorheology: cure time (s)[1] | 16 | 8 | | 29 |
| Photorheology: G' (KPa)[1] | 50 | 9 | | 27 |
| WCA | 71 | | 87 | |
| Modulus (MPa) | 0.93 | | | |
| Max. Elongation | 298 | | | |
| $Dk_c$ (barrer) | 171 | | | |
| Ion permeability[3] | 21.2 | | | |

Example 8

A: Chain-Extended PDMS Cross-Linker with Pendant p(DMA) Chains

Mono-dihydroxyl terminated poly(N,N-dimethylacrylamide) (poly(DMA)) is prepared by radical polymerization

TABLE 7

| | M.W. of hydrophile/PDMS | Stoichiometric ratio: branched hydrophile: PDMS | Structure |
|---|---|---|---|
| Crosslinker 5 | 6000/4500 | 2:3 | 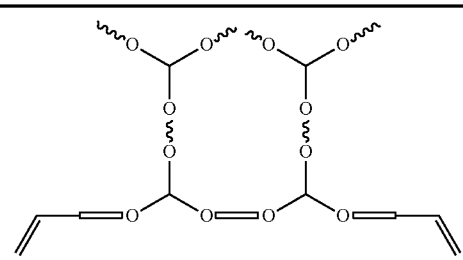 |
| Crosslinker 6 | 4500/4500 | 2:3 | | using 3-mercapto-1,2-propanediol as chain transfer reagent, as shown in the following scheme

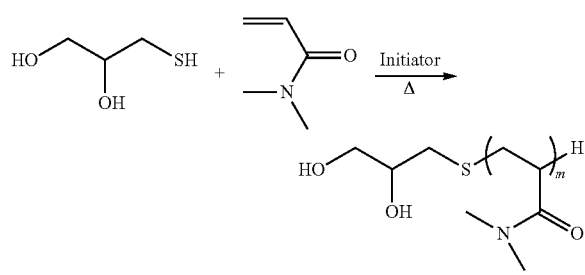

In a typical experiment, DMA (15.861 g, 160 mmol), AIBN (0.263 g, 1.44 wt % of monomers), 3-mercapto-1,2-propanediol (2.388 g, 22.08 mmol), and toluene (42.80 mL) are introduced into a 250 mL Pyrex round flask. The solution is purged with $N_2$ gas for 30 min before polymerization is carried out at 65° C. for 12 h. The product is dialyzed in 2 L toluene using MWCO 500 Cellulose Ester (Spectra/Por® Biotec) tube for 12 hours. The final product is precipitated into ethyl ether, decanted, and dried under vacuum. The number average molecular weight of the final polymer was 383 g/mol based on GPC using THF as the eluent and polystyrene as the standards.

Intermediary copolymers having PDMS segments and pendant poly(DMA) chains and terminated with isocyanate group is synthesized via condensation reaction between a mono-bishydroxyl terminated poly(DMA) (4.50 g) prepared above and di-hydroxyl terminated PDMS (7.00 g) in presence of 1,6-hexamethylene diisocyanate (2.51 g) and catalytical amount of Dibutyltindilaurate (DBTDL) (0.075%) in 14 g of toluene at 40° C. for 2 hours. Reactions are allowed to proceed until percentage of NCO by titration is close to theoretically predicted values.

Isocyanate terminated intermediary copolymers are then converted to a crosslinker in a second step through reaction with N-hydroxylethyl acrylamide (HEAA) (0.69 g) at room temperature for 5-6 hrs. The resulting crosslinkers are dialyzed in methanol followed by ethyl acetate using MWCO 3,500 regenerator cellulose tube. Final crosslinker is kept in solution with OH-TEMPO inhibitor (100 ppm against the polymer). The number average molecular weight of the final polymer is 7,160 g/mol based on GPC using THF as the eluent and polydimethylsiloxane as the standards.

B: Chain-Extended PDMS Cross-Linker with Pendant p(DMA) Chains 44.46 g (448.0 mmol) of DMA, 0.184 g (1.12 mmol) of AIBN, 6.726 g, (61.82 mmol) of 3-mercapto-1,2-propanediol, 102.6 g of Toluene and 10.29 g of ethyl acetate are introduced into a 250 ml round flask. After degassing by nitrogen bubbling for 1.0 h, polymerization is carried out at 55° C. for 12 h. The product is dialyzed in toluene using MWCO 500 Cellulose Ester (Spectra/Por® Biotec) tube for 12 h. Final product is precipitated into hexane, decanted, and dried under vacuum. The number average molecular weight of the final polymer is 541 g/mol based on GPC using THF as the eluent and polystyrene as standards.

To dried 250 ml flask, 28.0 g (29.3 mmol) of purified Shin-Etsu 160AS, 24.0 g (29.0 mmol) of mono-dihydroxyl terminated poly(DMA) above prepared and 64.0 g toluene are added. The flask is placed in 40° C. oil bath with stirring until dissolution. After cooling down to room temperature, 11.81 g (69.88 mmol) of hexamethylene diisocyanate with 3 drops of Dibutyltindilaurate (DBTDL) are added. Reaction is preceded in 40° C. oil bath for about 2 hrs and NCO conversion is monitored by titration until close to theoretical value. Cooled down again to room temperature and then 3.256 g (27.95 mmol) of HEAA is added with 3 drops catalyst to react overnight. Product is dialyzed in methanol and ethyl acetate, respectively using MWCO 3,500 regenerator cellulose tube. Final macromer is kept in solution with H-tempo inhibitor for solid content determination, formulation and lens fabrication. The number average molecular weight of the final polymer is 7,464 g/mol based on GPC using THF as the eluent and polydimethylsiloxane as the standards.

C. Formulation and Lens Casting

Formulations are prepared by dissolving a chain-extended PDMS crosslinker with pendant p(DMA) chains in dipropylene glycol methyl ether (DPGME) to have a concentration of about 60% by weight. Each formulation also contains 0.3% by weight of Irgacure 2959. Typical conditions for formulation photo-rheology and lens production are about 4-10 seconds at 4-6 mW/cm$^2$ with 297 nm filter cut off depended on mold type used. The molded lenses are characterized and properties are reported in Table 9.

TABLE 9

| Properties | Crosslinker A | Crosslinker B |
|---|---|---|
| G' (kPa) | 131 | 164 |
| Curing time (s) | 6 | 4 |
| Viscosity (mPa · S) | 2,820 | 4,130 |
| Modulus (MPa) | 1.05 | 1.07 |
| Maximum Elongation (%) | 217 | 209 |
| Dkc (Barrer) | 125 | 83 |
| IP (relative to Alsacon) | 0.9 | 7.6 |
| Water % | 34 | 39 |
| Lubricity | — | 2 |

D: Mold Cleaning

All above formulations are used for mold cleaning study. After lenses are made using the Quartz mold, the mold is rinsed with tap water. The mold is then examined with OptiSpec microscope. In most cases, the molds are efficiently cleaned.

Example 9

A one-liter reaction vessel is evacuated overnight to remove moisture, and the vacuum broken with dry nitrogen. 73.59 g (75 meq) of dried X-22-160AS (α,ω-bis(2-hydroxyethoxypropyl)-polydimethylsiloxane, M.W. ~1000, from Shin-Etsu) is charged to the reactor and then about 26.68 g (120 meq) of freshly distilled isophorone diisocyanate (IPDI) is added into the reactor. The reactor is purged with nitrogen and heated to 45° C. with stirring and then about 0.30 g of dibutyltin dilaurate (DBTDL) is added. The reactor is sealed, and a positive flow of nitrogen is maintained. An exotherm occurs, after which the reaction mixture is allowed to cool and stir at 55° C. for 2 hours. About 23.89 g (21.96 meq) of dried Ymer™ N120 (mono-3,3-bis(hydroxymethyl)butyl- and mono-methoxy-terminated polyethylene glycol, M.W. ~1000, from Perstorp Polyols, Inc.) is added to the reactor at 55° C., followed by 100 µL of DBTDL. The reaction is continued for 2 hours before heating is discontinued and the reactor is allowed to cool. About 6.59 g (50.64 meq) of 2-hydroxyethyl methacrylate (HEMA) is added to the reactor, along with 100 µL of DBTDL. The reaction is continued under dry air with moderate stirring for 24 hours, leading to formation of hydrophilized chain-extended polysiloxane crosslinkers (YSX-75) having the formula of

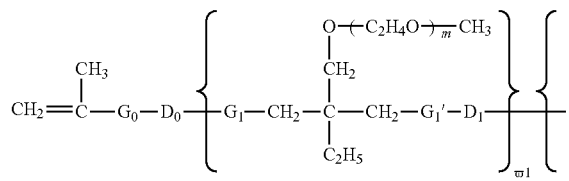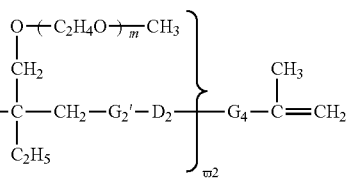

in which $G_0$ and $G_4$ are a divalent radical of $C(O)-O-C_2H_4-O-C(O)-NH-Z_3-NH-C(O)-O-$ and $-O-C(O)-NH-Z_3-NH-C(O)-O-C_2H_4-O-C(O)-$ respectively, in which $Z_3$ is a divalent radical of

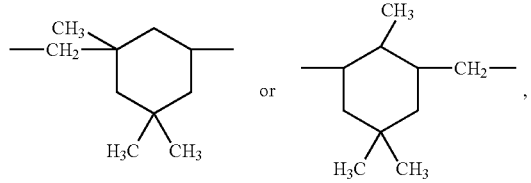

$D_0$, $D_1$, and $D_2$ are a divalent radical of

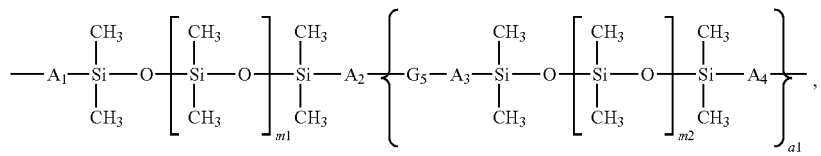

$G_1$, $G_1'$, $G_2$, and $G_2'$, and G5 independent of one another are $-O-C(O)-NH-Z_3NH-C(O)-O-$ in which $Z_3$ is as defined above, $A_1$ and $A_3$ are $-C_2H_4OC_3H_6-$, $A_2$ and $A_4$ are $-C_3H_6OC_2H_4-$, m is an integer of about 15 to 29, m1 and m2 independent of each other are an integer of about 7 to about 14, a1 is an integer of 0 to 9, ω1 and ω2 independent of each other are an integer of 0 to 10. The number average molecular weight of YSX-75 is determined to be about 17,000 Daltons based on conventional GPC using DMF as the eluent and polystyrene as the standard. The product is decanted and stored under refrigeration.

Example 10

Copolymer/Macromer Synthesis

A 500-mL jacketed reactor is equipped with a heating/chilling loop, septum inlet adapter, reflux condenser with $N_2$-inlet adapter, vacuum line and overhead stirring. 25.6 g of hydrophilized chain-extended PDMS crosslinker (YSX-75, prepared in Example 9), is prepared as a 50% solution in t-amyl alcohol and then charged to the reaction vessel. The solution is degassed under vacuum less than 1 mBar for 5 minutes, and then re-pressurizing with dry nitrogen. This degas procedure is repeated for a total of 6 times.

A monomer solution is prepared by dissolving 5.76 g of methyl bis(trimethylsiloxy)silyl]propyl glycerol methacrylate (SiGMA), 1.50 g of methacrylic acid, 13.67 g of N,N-dimethylacrylamide and 1.23 g of aminopropyl methacrylamide hydrochloride salt in a mixture of 1.23 g of DI water and 175 g of t-amyl alcohol. This monomer solution is transferred to an additional funnel sitting on top of reaction vessel followed with a degas process under vacuum at 100 mBar for 10 minutes, and then re-pressurizing with dry nitrogen. This degas procedure is repeated for a total of 3 times.

An initiator and chain-transfer agent (CTA) pot solution is prepared by mixing 0.15 g of azo-bis(isobutyronitrile) pre-dissolved in 37.50 g of t-Amyl alcohol and 0.755 g of cysteamine hdrochloride pre-dissolved in 0.60 g of DI water and 1.80 g of methanol is degassed under vacuum at 100 mBar for 10 minutes, and then re-pressurizing with dry nitrogen. This degas procedure is repeated for a total of 3 times.

The CTA feed solution is prepared by dissolving 1.136 g of cysteamine hydrochloride in 0.90 g of DI water, 2.25 g of methanol and 56.25 g of t-amyl alcohol.

After both YSX-75 solution and monomer solution are degassed, the monomer solution is charged to the reaction vessel. Temperature of the mixed solution is then quickly elevated from room temperature to 64° C. The initiator/CTA solution is injected to the system when the temperature close to 64° C. and CTA feed solution is fed over 2 hours through a combination of degas unit and HPLC pump. The reaction mixture is maintained at 64° C. under nitrogen for 5 hours after the initiator solution is injected. After the copolymerization is done and the temperature is cooled to room temperature, the reaction solvent is exchanged to isopropyl alcohol and then to water as a 2 liter solution. The copolymer solution is purified by ultrafiltration and then charged to a 2-L reactor equipped with overhead stirring, refrigeration loop, thermometer, and the pH meter and dispensing tip of a Metrohm Model 718 STAT Titrino. The reaction mixture is then cooled to 1° C. 4.8 g of $NaHCO_3$ are charged to the solution and stirred to dissolve. The Titrino is set to maintain pH at 9.5 by intermittent addition of 20% sodium hydroxide solution. Acryloyl chloride, 9.6 mL, is then added over 2 hour using a syringe pump. After the solution is stirred for another hour, the Titrino is set to neutralize the reaction mixture by addition of a 2 N hydrochloric acid. The macromer solution is then filtered and then purified with ultrafiltration until the conductivity of permeability is less than 5 μS/cm. The purified macromer solution is then solvent exchanged to 1-propanol as a stock solution.

Formulation Composition and Photorheology:

| Formulation | | | Photorheology | | | |
|---|---|---|---|---|---|---|
| Macromer | Irgacur 2959 | Solvent DPGME | UV Intensity mW/cm² | Curing Time Seconds | G' kPa | Viscosity mPas |
| 60% | 0.3% | 39.7% | 6 | 13 | 150 | 6875 |
| 55% | 0.3% | 44.7% | 6 | 36 | 130 | 2500 |
| 55% | 0.5% | 44.5% | 6 | 19 | 115 | 2355 |

DPGME: dipropylene glycol methyl ether

Lens Fabrication:

The lenses are fabricated in polypropylene lens mold with equivalent UV energy as provided by photorheology. The lenses are demolded in DI water and then packed in saline solution followed with autoclave at 121° C. for 30 minutes.

Lens Characterization Properties:

| | Formulation | | Lens Characterization | | | |
|---|---|---|---|---|---|---|
| Macromer | Irgacur 2959 | Solvent DPGME | E' | EtB% | Dk | IP |
| 60% | 0.3% | 39.7% | 0.81 | 190% | 60 | 19 |
| 55% | 0.3% | 44.7% | 0.82 | 210% | 61 | 18 |
| 55% | 0.5% | 44.5% | 0.86 | 220% | 62 | 17 |

Example 11

Copolymer/Macromer Synthesis

The copolymer and macromer are prepared by the same manner as the macromer of Example 10 except that aminopropyl methacrylamide hydrochloride salt is not used as one of the monomers.

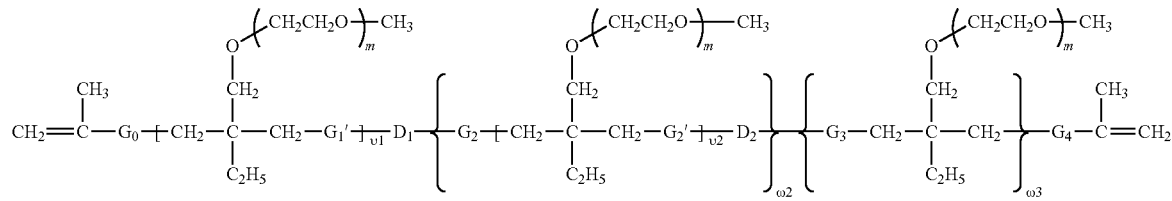

Formulation Composition and Photorheology:

| Formulation | | | Photorheology | | | |
|---|---|---|---|---|---|---|
| Macromer | Irgacur 2959 | Solvent DPGME | UV Intensity mW/cm² | Curing Time Seconds | G' kPa | Viscosity mPas |
| 60% | 0.3% | 39.7% | 6 | 38 | 89 | 14800 |

Lens Fabrication:

The lenses are fabricated according to the procedures described in Example 10.

Lens Characterization Properties:

| | Formulation | | Lens Characterization | | | |
|---|---|---|---|---|---|---|
| Macromer | Irgacur 2959 | Solvent DPGME | E' | EtB % | Dk | IP |
| 60% | 0.3% | 39.7% | 0.42 | 260% | 52 | 36 |

Example 12

A one-liter reaction vessel is evacuated overnight to remove moisture, and the vacuum broken with dry nitrogen. 73.59 g (75 meq) of dried X-22-160AS (α,ω-bis(2-hydroxyethoxypropyl)-polydimethylsiloxane, M.W. ~1000, from Shin-Etsu) is charged to the reactor and then about 39.23 g (176.5 meq) of freshly distilled isophorone diisocyanate (IPDI) is added into the reactor. The reactor is purged with nitrogen and heated to 45° C. with stirring and then about 0.30 g of dibutyltin dilaurate (DBTDL) is added. The reactor is sealed, and a positive flow of nitrogen is maintained. An exotherm occurs, after which the reaction mixture is allowed to cool and stir at 55° C. for 2 hours. About 72.12 g (66.20 meq) of dried Ymer™ N120 (mono-3,3-bis(hydroxymethyl) butyl- and mono-methoxy-terminated polyethylene glycol, M.W. 1000, from Perstorp Polyols, Inc.) is added to the reactor at 55° C., followed by 100 μL of DBTDL. The reaction is continued for 8 hours before heating is discontinued and the reactor is allowed to cool overnight. The nitrogen bubble is discontinued and the reactor is filled with dry air with moderate stirring. An α,ω-bis(isocyanate)-terminated chain extended polysiloxane having multiple segments of polysiloxane and pendent PEG 1000 chains is formed. About 9.83 g (75 meq) of 2-hydroxyethyl methacrylate (HEMA) is added to the reactor, along with 100 μL of DBTDL. The reaction is continued under dry air with moderate stirring for 24 hours, leading to a hydrophilized chain-extended polysiloxane crosslinker (YMER 50x) having the formula of in which $G_0$ and $G_4$ are respectively —C(O)—O—$C_2H_4$—O—C(O)—NH—$Z_3$—NH—C(O)—O— and —O—C(O)—NH—$Z_3$—NH—C(O)—O—$C_2H_4$—O—C(O)— in which $Z_3$ is a divalent radical of

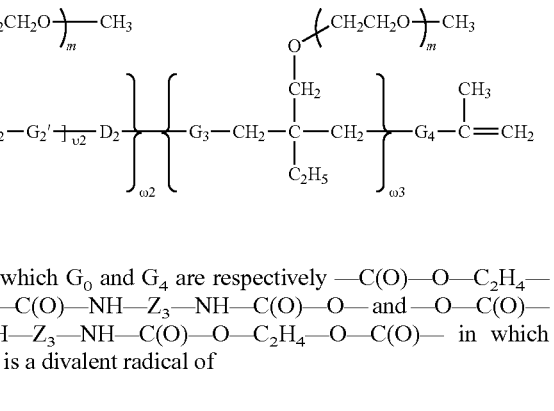

$G_1'$, $G_2$, $G_2'$, and $G_3$ independent of one another are —O—C(O)—NH—$Z_3$—NH—C(O)—O— in which $Z_3$ is as defined above, $D_1$ and $D_2$ are a divalent radical of

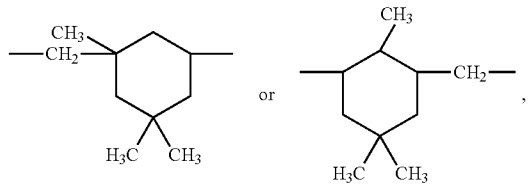

υ2 is an integer of 1 or 2, ω2 is an integer of 0 to about 10, υ1 and ω3 independent of each other is an integer of 0, 1 or 2, m is an integer of about 15 to 29, and m1 is an integer of about 7 to about 14. The number average molecular weight of YMER 50x is determined to be about 12,000 Daltons based on conventional GPC using DMF as the eluent and polystyrene as the standard. The product is decanted and stored under refrigeration.

What is claimed is:

1. A soluble amphiphilic prepolymer, which is obtained by:
   first polymerizing a polymerizable composition including
   (1) at least one chain-extended polysiloxane crosslinker,
   (2) at least one hydrophilic vinylic monomer,
   (3) a chain transfer agent with or without a first reactive functional group other than a thiol group and/or a vinylic monomer having a second reactive functional group other than an ethylenically unsaturated group,
   (4) optionally a hydrophobic vinylic monomer, and
   (5) optionally a polymerizable UV-absorbing agent, to form an intermediary copolymer; and
   then ethylenically functionalizing the intermediary copolymer with an ethylenically functionalizing vinylic monomer having a third reactive functional group capable of reacting with the first or second reactive functional group to form a linkage in a coupling reaction in the presence or absence of a coupling agent to form the prepolymer, wherein the first, second and third reactive functional groups independent of each other are selected from the group consisting of amino group, hydroxyl group, carboxyl group, acid halide group, azlactone group, isocyanate group, epoxy group, aziridine group, and combination thereof
   wherein the linear chain-extended polysiloxane crosslinker comprises (a) two terminal ethylenically unsaturated groups, (b) at least two polysiloxane segments, and (c) at least one dangling hydrophilic polymer chain covalently attached to a divalent organic radical separating said at least two polysiloxane segments, wherein the linear chain extended polysiloxane crosslinker is as set forth by formula (I)

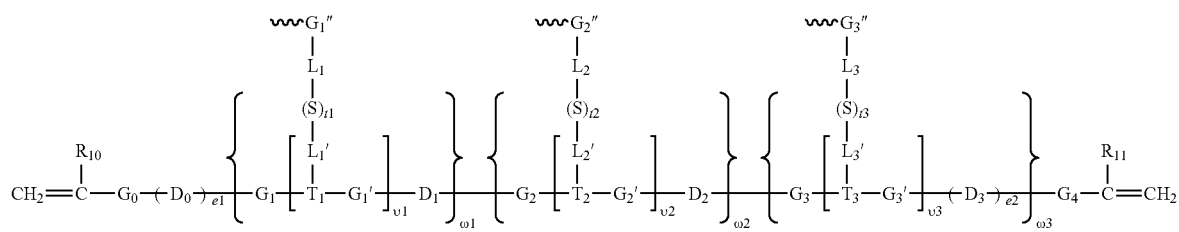

in which
$D_0$, $D_1$, $D_2$ and $D_3$ independently of one another are a divalent group of formula (II)

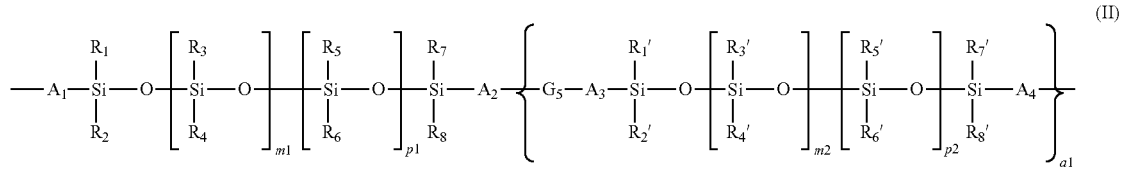

in which $G_5$ is as defined below, $A_1$, $A_2$, $A_3$, and $A_4$ independent of one another are a direct bond, a linear or branched $C_1$-$C_{10}$ alkylene divalent radical, —(CH(R")CH$_2$O)$_{r1}$—CH(R")CH$_2$— in which R" is H or methyl and r1 is an integer of 1 to 20, or a $C_1$-$C_7$ alkyleneoxy $C_1$-$C_7$ alkylene divalent radical, $R_1$, $R_2$, $R_3$, $R_4$, $R_5$, $R_6$, $R_7$, $R_8$, $R_1'$, $R_2'$, $R_3'$, $R_4'$, $R_5'$, $R_6'$, $R_7'$, and $R_8'$ independently of one another are $C_1$-$C_8$-alkyl, $C_1$-$C_4$ alkyl-substituted phenyl, $C_1$-$C_4$-alkoxy-substituted phenyl, fluoro($C_1$-$C_{18}$-alkyl), or -alk-(OCH$_2$CH$_2$)$_n$—OR$_9$ in which "alk" is $C_1$-$C_6$-alkylene divalent radical, $R_9$ is $C_1$-$C_6$ alkyl and n is an integer from 1 to 20, a1 is an integer of 0 to 8, m1 and p1 independently of each other are an integer of from 0 to 150, (m1+p1) is from 2 to 150, m2 and p2 independent of each other are an integer of from 0 to 150 and (m2+p2) is from 2 to 150 if a1 is not zero;
e1, e2, t1, t2, and t3 independent of one another are an integer of 0 or 1;
υ1, υ2 and υ3 independent of one another are an integer of from 0 to 5 provided that (υ1+υ2+υ3)≥1;
ω1, ω2 and ω3 independent of one another are an integer of from 0 to 20 provided that (ω1+ω2+ω3) is an integer of 1 to 20;
$L_1$, $L_2$ and $L_3$ independent of one another is a direct bond,

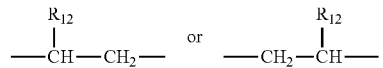

in which $R_{12}$ is hydrogen or $C_1$-$C_4$ alkyl;
$L_1'$, $L_2'$ and $L_3'$ independent of one another is a direct bond or

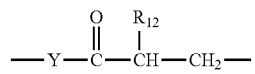

in which $R_{12}$ is as defined above, Y is —O— or —NR'— in which R' is hydrogen or $C_1$-$C_8$ alkyl, and Y is linked to $T_1$, $T_2$ or $T_3$;
$G_0$, $G_1$, $G_1'$, $G_1''$, $G_2$, $G_2'$, $G_2''$, $G_3$, $G_3'$, $G_3''$, $G_4$, and $G_5$ independent of one another are a direct bond or a divalent radical of —$Z_1$—$X_1$—$Z_2$—$X_2$—$Z_3$—$X_3$—$Z_4$—, in which $X_1$, $X_2$, and $X_3$ independent of one another are a linkage selected from the group consisting of a direct bond, —O—, —NR'—, —C(O)—NR'—, —NR'—C(O)—, —O—C(O)—NH—, —NH—C(O)—O—, —NR'—C(O)—NH—, —NH—C(O)—NR'—, —S—, —C(O)—O—, —O—C(O)—, —NH—C(O)—NH—$Z_0$—NH—C(O)—NH—, —O—C(O)—NH—$Z_0$—NH—C(O)—O—, —O—C(O)—NH—$Z_0$—NH—C(O)—NH—, and —NH—C(O)—NH—$Z_0$—NH—C(O)—O—, $Z_0$ is a linear or branched $C_2$-$C_{12}$ alkylene divalent radical or a $C_5$-$C_{45}$ cycloaliphatic or aliphatic-cycloaliphatic divalent radical optionally containing therein one or more linkages of —O—, —NR'—, —S— and —C(O)—, R' is H or $C_1$-$C_0$ alkyl, $Z_1$, $Z_2$, $Z_3$, and $Z_4$ independent of one another are a direct bond, a linear or branched $C_1$-$C_{18}$ alkylene divalent radical optionally containing therein one or more linkages of —O—, —NR'—, —S— and —C(O)—, a $C_1$-$C_7$ alkyleneoxy $C_1$-$C_7$ alkylene divalent radical, a divalent radical of —(CH(R")CH$_2$O)$_{r1}$—CH(R")CH$_2$— in which R" and r1 are as defined above, an unsubstituted phenylene divalent radical, $C_1$-$C_4$ alkyl substituted phenylene divalent radical, $C_1$-$C_4$ alkoxy substituted phenylene divalent radical, a $C_5$-$C_{45}$ cycloaliphatic or aliphatic-cycloaliphatic divalent radical optionally containing therein one or more linkages of —O—, —NR'—, —S— and —C(O)—, a $C_6$-$C_{24}$ aromatic or araliphatic divalent radical, or combinations thereof;

$R_{10}$ and $R_{11}$ independent of each other are hydrogen or $C_1$-$C_4$ alkyl;

∿∿∿ is a linear or 3-arm hydrophilic polymer chain that comprises at least about 60% by weight of one or more hydrophilic monomeric units; and $T_1$, $T_2$ and $T_3$ independent of one another are a linear or branched $C_2$-$C_{24}$ aliphatic trivalent radical, a $C_5$-$C_{30}$ cycloaliphatic or aliphatic-cycloaliphatic trivalent radical, a $C_4$-$C_{30}$ aliphatic-heterocyclic trivalent radical including one or more oxygen or nitrogen atoms, or a $C_3$-$C_{24}$ aromatic or araliphatic trivalent radical.

2. The prepolymer of claim 1, wherein the polymerizable composition comprises the polymerizable UV-absorbing agent.

3. An ophthalmic lens, comprising a silicone hydrogel material that is obtained by curing, in a mold, a lens-forming composition including a linear chain-extended polysiloxane crosslinker comprising (a) two terminal ethylenically unsaturated groups, (b) at least two polysiloxane segments, and (c) at least one dangling hydrophilic polymer chain covalently attached to a divalent organic radical separating said at least two polysiloxane segments, wherein the linear chain extended polysiloxane crosslinker is as set forth by formula (I)

in which $G_5$ is as defined below, $A_1$, $A_2$ $A_3$, and $A_4$ independent of one another are a direct bond, a linear or branched $C_1$-$C_{10}$ alkylene divalent radical, —(CH(R")CH$_2$O)$_{r1}$—CH(R")CH$_2$— in which R" is H or methyl and r1 is an integer of 1 to 20, or a $C_1$-$C_7$ alkyleneoxy $C_1$-$C_7$ alkylene divalent radical, $R_1$, $R_2$, $R_3$, $R_4$, $R_5$, $R_6$, $R_7$, $R_8$, $R_1'$, $R_2'$, $R_3'$, $R_4'$, $R_5'$, $R_6'$, $R_7'$, and $R_8'$ independent of one another are $C_1$-$C_8$-alkyl, $C_1$-$C_4$ alkyl-substituted phenyl, $C_1$-$C_4$-alkoxy-substituted phenyl, fluoro($C_1$-$C_{18}$-alkyl), or -alk-(OCH$_2$CH$_2$)$_n$—OR$_9$ in which "alk" is $C_1$-$C_6$-alkylene divalent radical, $R_9$ is $C_1$-$C_6$ alkyl and n is an integer from 1 to 20, a1 is an integer of 0 to 8, m1 and p1 independently of each other are an integer of from 0 to 150, (m1+p1) is from 2 to 150, m2 and p2 independent of each other are an integer of from 0 to 150 and (m2+p2) is from 2 to 150 if a1 is not zero;

e1, e2, t1, t2, and t3 independent of one another are an integer of 0 or 1;

υ1, υ2 and υ3 independent of one another are an integer of from 0 to 5 provided that (υ1+υ2+υ3)≥1;

ω1, ω2 and ω3 independent of one another are an integer of from 0 to 20 provided that (ω1+ω2+ω3) is an integer of 1 to 20;

$L_1$, $L_2$ and $L_3$ independent of one another is a direct bond,

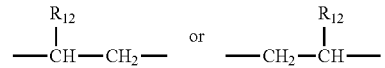

in which $R^{12}$ is hydrogen or $C_1$-$C_4$ alkyl;

$L_1'$, $L_2'$ and $L_3'$ independent of one another is a direct bond or

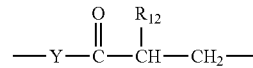

(I)

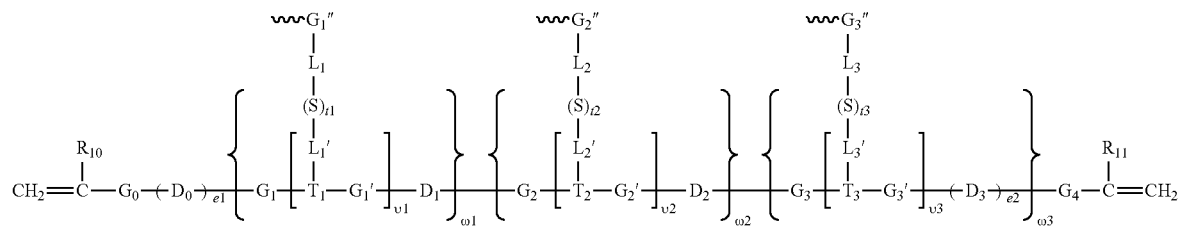

in which $D_0$, $D_1$, $D_2$ and $D_3$ independently of one another are a divalent group of formula (II)

in which $R_{12}$ is as defined above, Y is —O— or —NR'— in which R' is hydrogen or $C_1$-$C_8$alkyl, and Y is linked to $T_1$, $T_2$ or $T_3$;

(II)

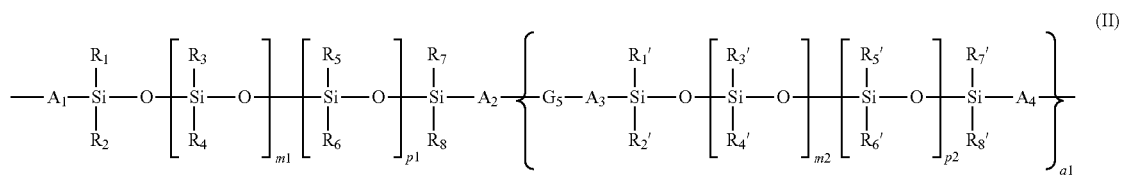

$G_0$, $G_1$, $G_1'$, $G_1''$, $G_2$, $G_2'$, $G_2''$, $G_3$, $G_3'$, $G_3''$, $G_4$, and $G_5$ independent of one another are a direct bond or a divalent radical of —$Z_1$—$X_1$—$Z_2$—$X_2$—$Z_3$—$X_3$—$Z_4$—, in which $X_1$, $X_2$, and $X_3$ independent of one another are a linkage selected from the group consisting of a direct bond, —O—, —NR'—, —C(O)—NR'—, —NR'—C(O)—, —O—C(O)—NH—, —NH—C(O)—O—, —NR'—C(O)—NH—, —NH—C(O)—NR'—, —S—, —C(O)—O—, —O—C(O)—, —NH—C(O)—NH—$Z_0$NH—C(O)—NH—, —O—C(O)—NH—$Z_0$—NH—C(O)—O—, —O—C(O)—NH—$Z_0$—NH—C(O)—NH—, and —NH—C(O)—NH—$Z_0$—NH—C(O)—O—, $Z_0$ is a linear or branched $C_2$-$C_{12}$ alkylene divalent radical or a $C_5$-$C_{45}$ cycloaliphatic or aliphatic-cycloaliphatic divalent radical optionally containing therein one or more linkages of —O—, —NR'—, —S— and —C(O)—, R' is H or $C_1$-$C_8$ alkyl, $Z_1$, $Z_2$, $Z_3$, and $Z_4$ independent of one another are a direct bond, a linear or branched $C_1$-$C_{18}$ alkylene divalent radical optionally containing therein one or more linkages of —O—, —NR'—, —S— and —C(O)—, a $C_1$-$C_7$ alkyleneoxy $C_1$-$C_7$ alkylene divalent radical, a divalent radical of —(CH(R")CH$_2$O)$_{r1}$—CH(R")CH$_2$— in which R" and r1 are as defined above, an unsubstituted phenylene divalent radical, $C_1$-$C_4$ alkyl substituted phenylene divalent radical, $C_1$-$C_4$ alkoxy substituted phenylene divalent radical, a $C_5$-$C_{45}$ cycloaliphatic or aliphatic-cycloaliphatic divalent radical optionally containing therein one or more linkages of —O—, —NR'—, —S— and —C(O)—, a $C_6$-$C_{24}$ aromatic or araliphatic divalent radical, or combinations thereof;

$R_{10}$ and $R_{11}$ independent of each other are hydrogen or $C_1$-$C_4$ alkyl;

 is a linear or 3-arm hydrophilic polymer chain that comprises at least about 60% by weight of one or more hydrophilic monomeric units; and $T_1$, $T_2$ and $T_3$ independent of one another are a linear or branched $C_2$-$C_{24}$ aliphatic trivalent radical, a $C_5$-$C_{30}$ cycloaliphatic or aliphatic-cycloaliphatic trivalent radical, a $C_4$-$C_{30}$ aliphatic-heterocyclic trivalent radical including one or more oxygen or nitrogen atoms, or a $C_3$-$C_{24}$ aromatic or araliphatic trivalent radical, wherein the lens-forming composition further comprises one or more components selected from the group consisting of a hydrophilic vinylic monomer, a hydrophobic vinylic monomer, a polysiloxane-containing vinylic monomer, a polysiloxane-containing vinylic macromer, a crosslinking agent having a molecular weight of less than 700 Daltons, a polymerizable UV-absorbing agent, a visibility tinting agent, an antimicrobial agent, a bioactive agent, a leachable lubricant, a leachable tear-stabilizing agent, and mixtures thereof, wherein the ophthalmic lens has at least one property selected from the group consisting of: an oxygen permeability of at least about 40 barrers; an elastic modulus of from about 0.1 MPa to about 2.0 MPa; an Ionoflux Diffusion Coefficient, D, of, at least about $1.0 \times 10^{-5}$ mm$^2$/min; a water content of from about 15% to about 55% by weight when fully hydrated; and combinations thereof.

4. An ophthalmic lens, comprising a silicone hydrogel material that is obtained by curing a lens-forming composition including a soluble amphiphilic prepolymer of claim 1 in a mold, wherein the lens-forming composition further comprises one or more components selected from the group consisting of a hydrophilic vinylic monomer, a hydrophobic vinylic monomer, a polysiloxane-containing vinylic monomer, a polysiloxane-containing vinylic macromer, a crosslinking agent having a molecular weight of less than 700 Daltons, a polymerizable UV-absorbing agent, a visibility tinting agent, an antimicrobial agent, a bioactive agent, a leachable lubricant, a leachable tear-stabilizing agent, and mixtures thereof, wherein the ophthalmic lens has at least one property selected from the group consisting of: an oxygen permeability of at least about 40 barrers; an elastic modulus of from about 0.1 MPa to about 2.0 MPa; an Ionoflux Diffusion Coefficient, D, of at least about $1.0 \times 10^{-5}$ mm$^2$/min; a water content of from about 15% to about 55% by weight when fully hydrated; and combinations thereof.

5. An ophthalmic lens, comprising a silicone hydrogel material that is obtained by curing a lens-forming composition including a soluble amphiphilic prepolymer of claim 2 in a mold, wherein the lens-forming composition further comprises one or more components selected from the group consisting of a hydrophilic vinylic monomer, a hydrophobic vinylic monomer, a polysiloxane-containing vinylic monomer, a polysiloxane-containing vinylic macromer, a crosslinking agent having a molecular weight of less than 700 Daltons, a polymerizable UV-absorbing agent, a visibility tinting agent, an antimicrobial agent, a bioactive agent, a leachable lubricant, a leachable tear-stabilizing agent, and mixtures thereof, wherein the ophthalmic lens has at least one property selected from the group consisting of: an oxygen permeability of at least about 40 barrers; an elastic modulus of from about 0.1 MPa to about 2.0 MPa; an Ionoflux Diffusion Coefficient, D, of at least about $1.0 \times 10^{-5}$ mm$^2$/min; a water content of from about 15% to about 55% by weight when fully hydrated; and combinations thereof.

\* \* \* \* \*